United States Patent [19]
Scherer et al.

[11] 4,013,452
[45] Mar. 22, 1977

[54] UREA DERIVATIVES AND THEIR USE AS HERBICIDES

[75] Inventors: Otto Scherer, Bad Soden, Taunus; Gerhard Horlein, Frankfurt am Main; Hubert Schonowsky, Neu-Isenburg, all of Germany

[73] Assignee: Hoechst Aktiengesellschaft, Frankfurt am Main, Germany

[22] Filed: July 21, 1975

[21] Appl. No.: 597,671

Related U.S. Application Data

[60] Division of Ser. No. 40,704, May 26, 1970, Pat. No. 3,937,726, which is a continuation-in-part of Ser. No. 628,843, April 6, 1967, abandoned, and Ser. No. 799,088, Feb. 13, 1969, abandoned, and Ser. No. 800,748, Feb. 19, 1969, abandoned.

[52] U.S. Cl. .............................................. 71/120
[51] Int. Cl.² ...................................... A01N 9/20

[58] Field of Search ................. 71/120; 260/553 A

[56] References Cited

UNITED STATES PATENTS

| 2,655,445 | 10/1953 | Todd .................................... 71/120 |
| 2,655,534 | 10/1953 | Searle .................................... 71/99 |
| 3,205,258 | 9/1965 | Simonian et al. ..................... 71/120 |
| 3,385,690 | 5/1968 | Luckenbaugh ....................... 71/120 |

FOREIGN PATENTS OR APPLICATIONS

| 1,520,220 | 2/1968 | France ................................ 71/120 |

*Primary Examiner*—Glennon H. Hollrah
*Attorney, Agent, or Firm*—Curtis, Morris & Safford

[57] ABSTRACT

Method of controlling weeds in cotton with fluoroalkoxy ureas.

4 Claims, No Drawings

UREA DERIVATIVES AND THEIR USE AS HERBICIDES

This is a divisional application of application Ser. No. 40,704 filed May 26, 1970, now U.S. Pat. No. 3,937,726 granted Feb. 10, 1976, which in turn is a continuation-in-part application of applications Ser. No. 628,843 filed Apr. 6, 1967, Ser. No. 799,088 filed Feb. 13, 1969, and Ser. No. 800,748 filed Feb. 19, 1969, all now abandoned.

The present invention relates to novel derivatives of the general formula

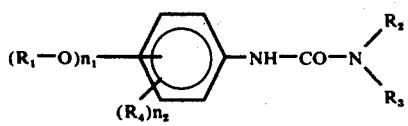

in which $R_1$ stands for a haloalkyl, halocycloalkyl, haloalkenyl or halocycloalkenyl radical each having 2 to 5 carbon atoms, the halogen being fluorine, chlorine and/or bromine, $n_1$ is 1 or 2, $R_4$ stands for a halogen atom, the trifluoromethyl-radical or for an alkyl- or alkoxy-radical with 1 to 3 carbon atoms, $n_2$ is 0, 1, 2 or 3, $R_2$ stands for a hydrogen atom or an alkyl radical with 1 to 4 carbon atoms and $R_3$ stands for an alkyl- or alkoxy-radical each having 1 to 4 carbon atoms.

The specified compounds are obtained by reacting
1. halogenoalkoxy-arylisocyanates or halogenoalkoxy-aryl-carbamic acid chlorides with
   a. alkyl- or dialkyl-amines or O-alkyl- or O,N-dialkylhydroxylamines or
   b. O-alkylhydroxyl-amines with subsequent alkylation or
   c. N-alkylhydroxyl-amines with subsequent alkylation or
   d. hydroxyl-amine with subsequent dialkylation; or reacting
2. halogenoalkoxy-arylamines with alkylisocyanates or di-alkylcarbamic acid chlorides.

The compounds can be prepared, for example, in one of the following ways:

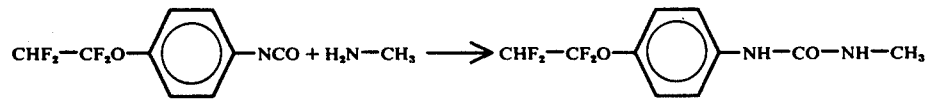

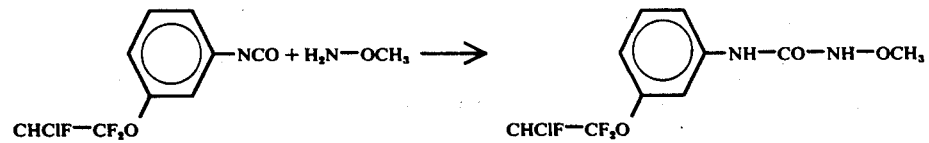

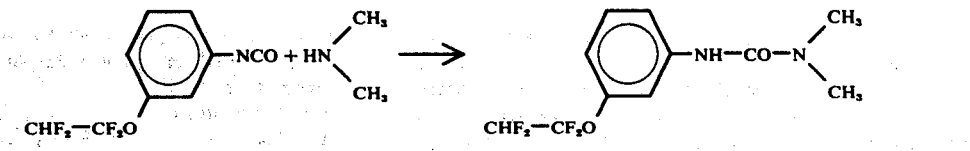

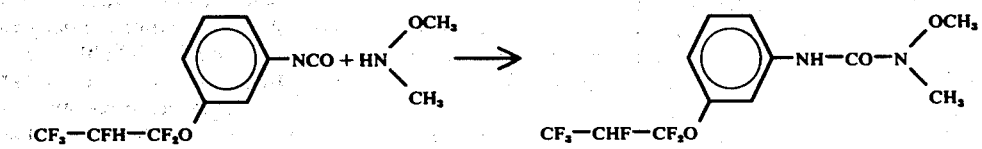

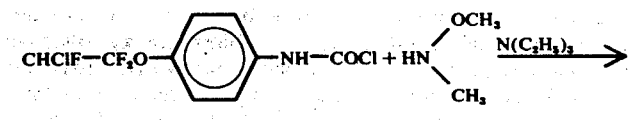

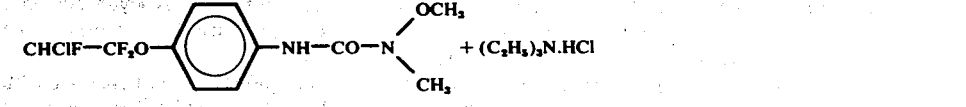

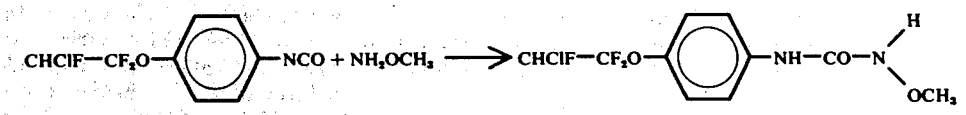

-continued

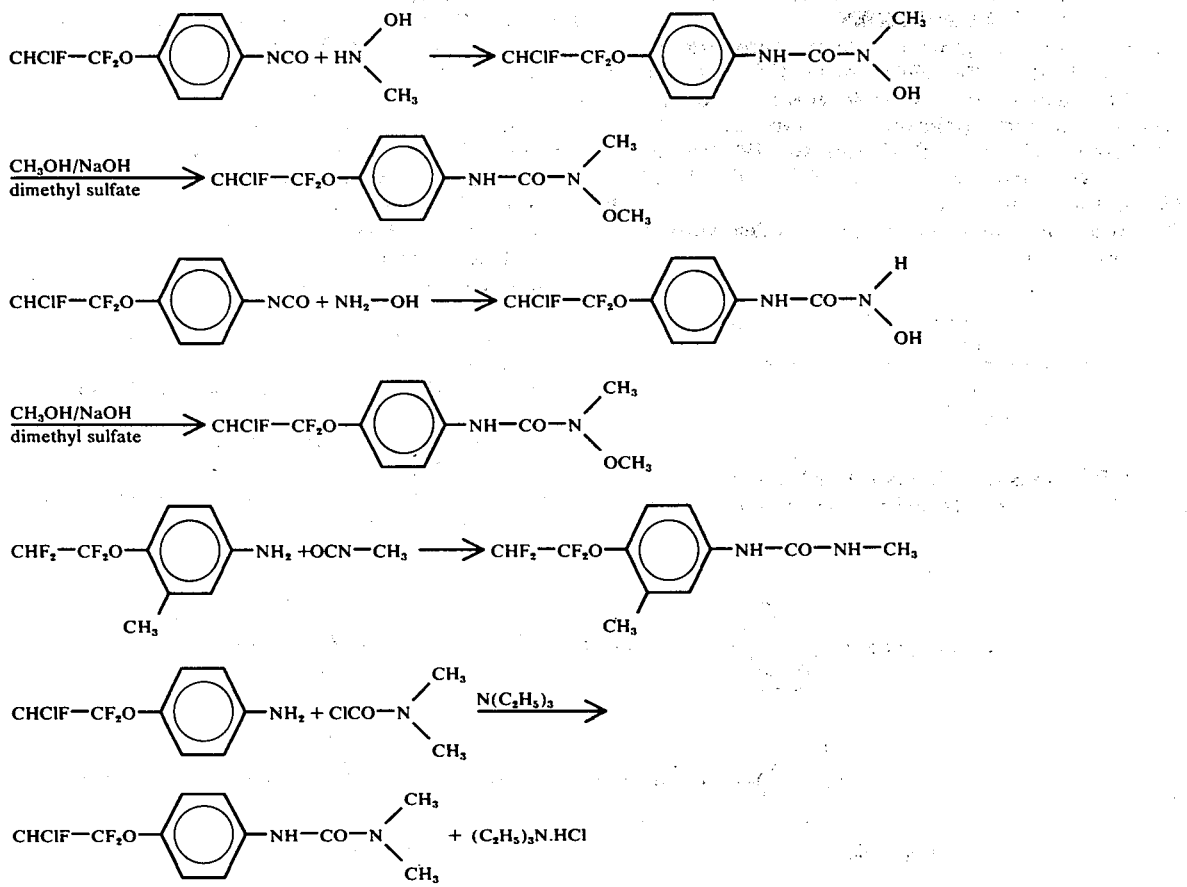

The reactions of the halogenoalkoxy-arylisocyanates or carbamic acid chlorides with the amines or alkylated hydroxylamines are preferably carried out at a temperature below 80° C in the presence of absence of a diluent. Suitable diluents are, for example, benzene, toluene, dioxane or dimethyl formamide.

The corresponding reactions with hydroxylamine are advantageously performed at a temperature below 40° C, in a two-phase mixture of water and an organic solvent immiscible with water.

The alkylations are suitably carried out in aqueous-alkaline suspension or in mixtures of aqueous alkali and an organic solvent. The alkali metal hydroxide solution and the alkylating agent are advantageously added simultaneously. Alternatively, the urea may be placed first in the reaction vessel together with the alkylating agent in an organic solvent and the alkali metal hydroxide solution may then be added or, in the case of compounds that are less sensitive towards alkali, the order of addition may be reversed. The reaction temperature naturally depends on the reactivity of the alkylating agents used and is in the range from 10° to 90° C.

The alkylations in processes (1b), (1c), and (1d) are carried out with dialkyl-sulfates, alkyl halides or alkyl-toluene-sulfonates. In (2) anilines carrying corresponding substituents are used.

Suitable starting compounds for processes (1a), (1b), (1c), and (1d) are, for example, 3- or 4-(1',1',2'-trifluoro-2'-chloro-ethoxy)-phenylisocyanate, 3-methyl-4-(1',1',2'-tri-fluoro-2'-chloro-ethoxy)-phenylisocyanate, 3- or 4-(1',1',2',2',-tetra-fluoro-ethoxy)-phenylisocyanate, 3-methyl-4-(1',1',2',2'-tetrafluoro-ethoxy)-phenylisocyanate, 3- or 4-(1',1',2',-3',3',3'-hexafluoro-propoxy)-phenylisocyanate, 3-methyl-4-(1',1',2',3', 3',3'-hexafluoro-propoxy)-phenylisocyanate, 3-(1',1',2'-tri-fluoro-ethoxy)-phenylisocyanate, 3- or 4-(1',1',2'-trifluoro-2'-bromo-ethoxy)-phenylisocyanate, 3-methyl-4-(1',1',2'-tri-fluoro-2'-bromo-ethoxy)-phenylisocyanate, 3- or 4-(1',1'-di-fluoro-2',2'-dichloro-ethoxy)-phenylisocyanate, 4-(3',3'-di-chloroallyloxy)-phenylisocyanate, 4-(2',3',3'-trichloroallyloxy)-phenylisocyanate, 4-(1',2'-dichlorovinyloxy)-phenylisocyanate, 3-chloro-4-(2'-chloroethoxy)-phenylisocyanate, 3-methyl-4-(2'-chloroethoxy)-phenylisocyanate and 3-trifluoromethyl-4-(2'-chloro-ethoxy)-phenylisocyanate and other analogous phenylisocyanates having in the $R_4$-position for example chloro- or bromo-, or the methyl-, methoxy-, ethyl- or propyl -radical.

Instead of the isocyanates phenylcarbamic acid chlorides carrying the corresponding substituents may also be used.

The novel isocyanates are obtained by phosgenation of the corresponding amines or the hydrochlorides which can be prepared by the following methods A, B, C and D. Method A consists in the reaction of alkali metal nitro-phenolates with halogenated alkenes (trichloroethylene, tribromoethylene, trichloropropene, tetrachloropropene), halogenated cycloalkenes (hexafluoro-dichloro-cyclopentene, tetrafluoro-dichloro-cyclobutene) and halogenated alkanes (1,1-di-fluoro-1,2,2-tri-ethane chloride etc.) analogous to (1) British patent specification 617 820; C.A. 43 (1949) 7045 et seq., (2) Ber. 96 (1963) 52, (3) Ind. Chem. 39 (1947)

412; and the subsequent catalytic reduction of the nitro-compound thus obtained.

The following examples serve to illustrate the reaction conditions.

EXAMPLE:

Preparation of the 3-(1',2'-dichlorovinyloxy)-aniline 161 grams (1 mole) of 3-nitrophenol sodium were dissolved in 400 milliliters of dimethyl formamide and 145 grams (1.1 mole) of trichloroethylene were dropped in at 60° C. Subsequently the mixture was stirred for 6 hours at 80° C. The main amount of dimethyl formamide was distilled off in vacuo. The oily residue was poured into ice water, was separated, dried over $Na_2SO_4$ and distilled.

$Kp_{0.01}mm$: 115° – 117° C; Yield: 115 grams of 3-(1',2'-dichlorovinyloxy)-nitrobenzene 1 mole of the nitro-product was dissolved in 1 liter of ethanol and was reduced by means of hydrogen in an autoclave at 60° C, after 5 grams of a Raney-nickel catalyst (R/50) had been added. The catalyst was then filtered off with suction, the ethanol was distilled off, and the residue was distilled in vacuo.

$Kp_{0.5}mm$: 116° – 118° C Yield: 121 grams of 3-(1',2'-dichlorovinyloxy)-aniline. Method B consists in the reaction of nitro- or acetamino-phenols with halogenated alkanes (1,1-difluoro-1,2,2-trichloro-ethane, 1,1,2-trifluoro-1,2-dibromoethane) and halogenated alkenes (trichloroethylene etc.) in the presence of $K_2CO_3$ analogous to (4) J. Am. Chem. Soc. 70 (1948) 593; and in the conversion of the nitro-compound into aniline, as described by Method A, or the cleavage of the acetamino compound into the aniline hydrochloride.

The following example serves to illustrate the process:

EXAMPLE:

Preparation of the 3-acetamino-(1',1'-difluoro-2',2'-dichloro)-phenetol.

151 grams (1 mole) of 3-acetamino-phenol were dissolved in 400 milliliters of dimethyl formamide, and 138 grams (1 mole) of $K_2CO_3$ were added, while stirring, 186 grams (1.1 mole) of 1,1-difluoro-1,2,2-trichloro-ethane were dropped into the mixture at 60° C; the mixture was maintained at 80° C for 6 hours and was then poured into about 4 liters of ice water. The precipitated crystalline product was filtered off with suction and dried.

Melting point: 72° – 74° C Yield: 281 grams of 3-acetamino-(1',1'-difluoro-2',2'-dichloro)-phenetol 1 mole of acetamino compound was dissolved in 2 liters of hydrochloric acid of 18% strength, while heating, and was maintained at 100° C for 2 hours. After cooling, the precipitated crystalline product was filtered off with suction and dried.

Melting point: 227° C; Yield: 230 grams of 3-(1',1'-difluoro-2',2'-dichloroethoxy)aniline hydrochloride.

Method C consists in the reaction of nitro-phenols or aminophenols, in particular 3-amino-phenol, with halogenated alkenes (tetrafluoro-ethylene, trifluoro-ethylene, trifluoro-chloroethylene, hexafluoro-propene, difluoro-dichloroethylene etc.) analogous to (5) J. Am. Chem. Soc. 73 (1951) 5831; (6) Bull. Soc. chim. France [5] 1957, 581; and the subsequent catalytic reduction, as described by Method A.

EXAMPLE:

Preparation of the 3-(1',1',2'-trifluoro-2'-chloroethoxy)-aniline.

139 grams (1 mole) of 3-nitro-phenol and 28 grams (0.5 mole) of potassium hydroxide were dissolved in 400 milliliters of dimethyl formamide, and 140 grams (1.2 mole) of trifluoro-chloroethylene were introduced in a gas pipe at 40° C; the mixture was then maintained at 60° C for 2 hours. The main amount of dimethyl formamide was distilled off in vacuo. The residue was poured into ice water, separated, dried over $Na_2SO_4$ and distilled in vacuo.

$Kp_{0.3}mm$: 89° – 90° C; Yield: 176 grams of 3-nitro-(1',1',2'-trifluoro-2'-chloro)-phenetol.

1 mole of the nitro-compound was reduced as described by Method A.

$Kp_{0.1}mm$: 86° C Yield: 171 grams of 3-(1',1',2'-trifluoro-2'-chloroethoxy)-aniline.

When in the example mentioned above 1 mole of 3-amino-phenol was used instead of 3-nitro-phenol, the 3-(1',1',2'-trifluoro-2'-chloroethoxy)-aniline was obtained directly. Method D consists in the reaction of nitro-phenolates with β-chloroethyl-p-toluene sulfonate analogous to (7) J. Chem. Soc. 121 (1922) 644, and the subsequent catalytic reduction of the nitro-products obtained into the anilines, as described by Method A.

EXAMPLE:

Preparation of the 4-(2'-chloroethoxy)-aniline 42 grams (1.05 mole) of sodium hydroxide were dissolved in 75 milliliters of water, and 139 grams (1 mole) of 4-nitrophenol and 235 grams (1 mole) of β-chloroethyl-p-toluene sulfonate were added, while stirring. Subsequently the reaction mixture was heated at 110° C for 4 hours. After cooling, the mixture was made alkaline by means of a solution of sodium hydroxide of 33% strength and was diluted with about 5 liters of water. The precipitated crystalline product was filtered off with suction, washed with water and dried.

Melting point: 54° – 55° C; Yield: 153 grams of 4-(2'-chloroethoxy)-nitrobenzene.

1 mole of the nitro-compound was reduced, as described by Method A.

Melting point: 66° C; Yield: 137 grams of 4-(2'-chloroethoxy)-aniline.

All alkoxy-anilines falling under the invention are obtained in accordance with the Methods A – D mentioned above by using in the pertinent exampler other corresponding substances with the same mole numbers, instead of the reactants mentioned therein. The following tables give a survey of the preparation and the properties of such amines.

Table 1

| Method | Nitro- and/or acetamino-compound | | Reactants | Kp/m.p. (mm) [°C] |
|---|---|---|---|---|
| A | HCCl=CClO—C6H4—NO2 | NaO—C6H4—NO2 | CCl2=CClH | 122 (0.3) |
| A | HCBr=CBrO—C6H4—NO2 | NaO—C6H4—NO2 | CBr2=CBrH | 192–196 (3) |
| A | HCCl=CClO—C6H3(CH3)—NO2 | NaO—C6H3(CH3)—NO2 | CCl2=CClH | 129–130 (0.4) |
| A | o-(OCF2—CCl2H)(NO2)C6H4 | m-NO2—C6H4—ONa | ClCF2—CCl2H | 103–108 (0.1) |
| C | m-(HCCl2—CF2O)(NO2)C6H4 | m-NO2—C6H4—OH | CF2=CCl2 | 108 (0.6) |
| A | (x) HCCl2—CF2O—C6H4—NO2 | NaO—C6H4—NO2 | ClCF2—CCl2H | 37–39 |
| C | HCCl2—CF2O—C6H3(CH3)—NO2 | HO—C6H3(CH3)—NO2 | CF2=CCl2 | 133–136 (λ) |

| Method | Aniline and/or hydrochloride | Kp/m.p. (mm) [°C] | Analysis calculated | found |
|---|---|---|---|---|
| A | HCCl=CClO—C6H4—NH2 | 120–123 (1) | 6.6% N  34.4% Cl | 6.9% N  34.1% Cl |
| A | HCBr=CBrO—C6H4—NH2 | 139 (0.2) | 4.8% N  54.6% Br | 4.7% N  54.3% Cl |
| A | HCCl=CClO—C6H3(CH3)—NH2 | 125–130 (0.5) | 6.5% N  32.9% Cl | 6.7% N  32.7% Cl |
| A | o-(OCF2—CCl2H)(NH2)C6H4 | 44–46 | 5.8% N  29.3% Cl | 6.0% N  29.1% Cl |

Table 1-continued

| Method | Nitro- and/or acetamino-compound | Reactants | | Kp/m.p. (mm) [° C] |
|---|---|---|---|---|
| C | 3-(HCCl$_2$—CF$_2$O)-aniline | 97 (0.3) | 5.8% N 29.3% Cl | 6.0% N 29.1% Cl |
| A | 4-(HCCl$_2$—CF$_2$O)-aniline | 50–51 | 5.8% N 29.3% Cl | 5.9% N 29.5% Cl |
| C | 4-(HCCl$_2$—CF$_2$O)-3-methyl-aniline | 111–114 (0.3) | 5.5% N 27.7% Cl | 5.6% N 27.4 Cl |

Table II

| Method | Nitro- and/or acetamino-compound | Reactants | | Kp/m.p. (mm) [° C] |
|---|---|---|---|---|
| B | 4-(HCCl$_2$—CF$_2$O)-3-methyl-acetanilide | 4-HO-3-methyl-acetanilide | Cl—CF$_2$—CCl$_2$H | 98 |
| A | 4-(HCCl$_2$—CF$_2$O)-2-methyl-5-chloro-nitrobenzene | 4-NaO-3-methyl-6-chloro-nitrobenzene | Cl—CF$_2$—CCl$_2$H | 36 |
| A | 4-(HCCl$_2$—CF$_2$O)-3-chloro-nitrobenzene | 4-NaO-3-chloro-nitrobenzene | Cl—CF$_2$—CCl$_2$H | 95 |
| A | 4-(HCCl$_2$—CF$_2$O)-3-chloro-nitrobenzene | 4-NaO-3-chloro-nitrobenzene | Cl—CF$_2$—CCl$_2$H | 95 |
| A | 4-(HCCl$_2$—CF$_2$O)-3-chloro-nitrobenzene | 4-NaO-3-methoxy-nitrobenzene | Cl—CF$_2$—CCl$_2$H | 45–47 |
| C | 4-(HClCF—CF$_2$O)-nitrobenzene (xx) | 4-HO-nitrobenzene | CF$_2$=CFCl | 117 (0.6) |

Table II-continued

| Method | Nitro- and/or acetamino-compound | Reactants | | Kp/m.p. (mm) [°C] |
|---|---|---|---|---|
| C | HClCF—CF$_2$O—(phenyl with NO$_2$, Cl) | HO—(phenyl with NO$_2$, Cl) | CF$_2$=CFCl | 105–108 (0.6) |
| C | HClCF—CF$_2$O—(phenyl with NO$_2$, CH$_3$) | HO—(phenyl with NO$_2$, CH$_3$) | CF$_2$=CFCl | 108–109 (0.3) |

| Method | Aniline and/or hydrochloride | Kp/m.p. (mm) [°C] | Analysis calculated | Analysis found |
|---|---|---|---|---|
| B | HCCl$_2$—CF$_2$O—(phenyl)—NH$_2$·HCl | 233 | 4.8% N<br>36.4% Cl | 4.6% N<br>36.0% Cl |
| A | HCCl$_2$—CF$_2$O—(phenyl with CH$_3$, Cl)—NH$_2$ | 135–138 (0.7) | 4.9% N<br>39.7% Cl | 4.7% N<br>36.3% Cl |
| A | HCCl$_2$—CF$_2$O—(phenyl with Cl)—NH$_2$ | 126–130 (0.5) | 5.1% N<br>38.5% Cl | 5.8% N<br>38.2% Cl |
| A | HCCl$_2$—CF$_2$O—(phenyl with CH$_3$O)—NH$_2$ | 136–140 (0.5) | 5.5% N<br>27.7% Cl | 5.8% N<br>27.9% Cl |
| C | (xx) HClCF—CF$_2$O—(phenyl)—NH$_2$ | 92–93 (0.5) | 6.2% N<br>15.7% Cl | 6.4% N<br>15.5% Cl |
| C | HClCF—CF$_2$O—(phenyl with Cl)—NH$_2$ | 159–162 (14) | 5.4% N<br>27.3% Cl | 5.6% N<br>27.5% Cl |
| C | HClCF—CF$_2$O—(phenyl with CH$_3$)—NH$_2$ | 91–93 (0.2) | 5.9% N<br>14.8% Cl | 5.7% N<br>14.5% Cl |

Table III

| Method | Nitro- and/or acetamino-compound | Reactants | | Kp/m.p. (mm) [°C] |
|---|---|---|---|---|
| C | 3-($H_2CF-CF_2O$)-nitrobenzene | 3-nitrophenol (HO-, -$NO_2$) | $CF_2=CFH$ | 86 (0.3) |
| C | — | 3-aminophenol (HO-, -$NH_2$) | $CF_2=CFH$ | → |
| C | (xxx) 3-($HCF_2-CF_2O$)-nitrobenzene | 3-nitrophenol | $CF_2=CF_2$ | 93 (2) |
| C | — | 3-aminophenol | $CF_2=CF_2$ | → |
| C | (xxx) 4-($HCF_2-CF_2O$)-nitrobenzene | 4-nitrophenol | $CF_2=CF_2$ | 42–44 |
| C | 4-($HCF_2-CF_2O$)-3-methyl-nitrobenzene | 4-hydroxy-3-methyl-nitrobenzene | $CF_2=CF_2$ | 86–88 (0.3) |
| C | 3-($CF_3-CFH-CF_2O$)-nitrobenzene | 3-nitrophenol | $CF_3-CF=CF_2$ | 77–79 (0.2) |

| Method | Aniline and/or hydrochloride | Kp/m.p. (mm) [°C] | Analysis calculated | found |
|---|---|---|---|---|
| C | 3-($H_2CF-CF_2O$)-aniline | 77–79 (0.6) | 7.3% N 29.8% F | 7.5% N 29.1% F |
| C | 3-($H_2CF-CF_2O$)-aniline | 75–76 (0.2) | 7.3% N 29.8% F | 7.6% N 29.0% F |
| C | (xxx) 3-($HCF_2-CF_2O$)-aniline | 65 (0.2) | 6.7% N 36.4% F | 6.8% N 36.7% F |

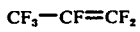

Table IV-continued

| | | | | |
|---|---|---|---|---|
| C | $CF_3-CFH-CF_2O-\phenyl-NH_2$ | 65–67 (0.2) | 5.4% N 44.0% F | 5.3% N 43.8% F |
| C | $CF_3-CFH-CF_2O-\phenyl(CH_3)-NH_2$ | 72–73 (0.3) | 5.1% N 41.7% F | 4.9% N 41.3% F |
| D | $ClCH_2-CH_2O-\phenyl(Cl)-NH_2$ | 62–63 | 6.8% N 34.5% Cl | 6.5% N 34.3% Cl |

(x) Compound described in Ber. 96 (1963) 52;
(xx) Compound described in Bull. Soc. Chim. France 5 1957, 581;
(xxx) Compound described in J. Org. Chem. 29 (1964) 5;

The novel urea derivatives of the invention are obtained in good yields. They constitute, almost exclusively, crystalline compounds. In most cases they may be used as they are obtained. Further purification by recrystallization from the usual organic solvents is also possible.

The novel compounds have a good action against weeds and are superior to known urea derivatives, for example, the chemically closely related N-(3-chloro-4-methoxyphenyl)-N'-methoxy urea (cf. U.S. Pat. No. 3,228,762) and metobromuron, in their preserving properties for a number of important crop plants such as maize, cotton, and legumes.

They are used in the form of wettable powders, emulsion concentrates, dusting powders or granules either alone, or, if desired, in combination with other herbicides, soil insecticides or with fertilizers.

Wettable powders are preparations that can be uniformly dispersed in water and contain, besides an inert substance, a wetting agent, for example ethoxylated alkylphenols, ethoxylated oleyl- or stearyl-amines, alkyl- or alkylphenylsulfonates and dispersing agents, for example the sodium salt of ligninsulfonic acid, 2,2'-dinaphthylmethane-6,6'-disulfonic acid, dibutyl-naphthalene-sulfonic acid or sodium oleylmethyltaurine.

Emulsion concentrates are obtained by dissolving the active ingredient in an organic solvent, for example butanol, cyclohexanone, dimethyl-formamide, xylene or aromatic hydrocarbons having a higher boiling point. To prepare good suspensions or emulsions in water wetting agents as specified above are further added.

Dusting powders are obtained by grinding the active ingredients with finely divided solid substances, for example talc, natural clays, pyrophillite or diatomaceous earth.

Granules can be prepared by atomizing the active ingredient on to an absorptive, granulated inert material, or by applying to the surface of granulated inert materials concentrates of the active ingredient with the aid of adhesives, for example polyvinyl alcohol, the sodium salt of polyacrylic acid or mineral oils. Alternatively, suitable active ingredients may be made into granules, if desired in admixture with fertilizers, in the manner commonly used for the manufacture of granulated fertilizers.

The novel compounds of the invention can be used in combination with the following known herbicides enumerated by

| | |
|---|---|
| urea derivatives | linuron, chloroxuron, monolinuron, fluometuron, diuron |
| triazine derivatives | simazin, atrazin, ametryne, prometryne, desmetryne, methoprotryne |
| urazil derivatives | lenacil, bromacil |
| pyrazone derivatives | 1-phenyl-4-amino-5-chloro-pyridazone (6) (PCA) |
| growth-promoting preparations | 2,4-dichlorophenoxy-acetic acid (2,4-D) 4-chloro-2-methylphenoxy-acetic acid (MCPA), 2,4,5-trichlorophenoxy-acetic acid (2,4,5-T), 4-chloro-2-methyl-phenoxy-butyric acid (MCPB), 2,3,6-trichlorobenzoic acid (TBA) |
| carbamic acid derivatives | barban, phenmedipham, triallate, diallate, vernolate and 2-chloro-allyl-N,N-diethyl-dithiocarbamate (CDEC) |
| dinitrophenol derivatives | dinitro-orthocresol (DNOC), di-nitro-sec.-butylphenol (DNBP), dinoseb acetate |
| chlorinated aliphatic acids | trichloroacetic acid, dalapon, diphenamide, N,N-diallyl-chloro-acetamide (CDAA) |
| dipyridilium compounds | paraquat, biquat, morfamquat |
| anilides | N-(3,4-dichlorophenyl)-methacryl-amide (DCMA), propanil, solan, monalide, |

| | |
|---|---|
| nitriles | dichlobenil, ioxynil |
| other preparations | flurenol |

When the active ingredients according to the invention are mixed with fertilizers, preparations are obtained which simultaneously have a fertilizing and a herbicidal effect.

EXAMPLE 1

Gaseous monomethylamine was introduced into a solution of 0.2 mole (50 grams) of 4-(1',1',2'-trifluoro-2'-chloroethoxy)-phenylisocyanate and 100 milliliters of petroleum ether at room temperature and whilst stirring until the solution was saturated. The reaction mixture was maintained for a further hour at 40° C, cooled, and the crystalline product was filtered off with suction and recrystallized from a large quantity of benzene.

Yield: 41 grams, melting point 150° – 152° C Analysis:

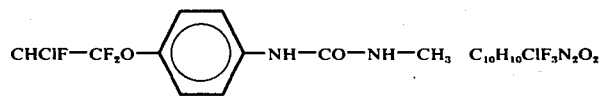

N-[4-(1',1',2'-trifluoro-2'-chloroethoxy)-phenyl]-N'-methyl-urea molecular weight 282.5 calculated 12.6% Cl 9.9% N found 12.5% Cl 10.1% N

EXAMPLE 2

0.1 mole (12 grams) of methylisocyanate was added at room temperature and whilst stirring to a solution of 0.2 mole (45 grams) of 4-(1',1',2'-trifluoro-2'-chloroethoxy)-aniline in 100 milliliters of absolute benzene. The reaction mixture was then heated for another 2 hours at 40° C. After cooling, the crystalline reaction product was filtered off with suction and recrystallized from a small quantity of n-propanol. Yield 35 grams, melting point 148° – 149° C. The mixed melting point with the compound prepared according to Example 1 did not show a depression.

EXAMPLE 3

0.1 mole (5 grams) of O-methylhydroxylamine was added at room temperature and with stirring to a solution of 0.1 mole (25 grams) of 4-(1',1',2'-trifluoro-2'-chloro-ethoxy)-phenylisocyanate in 120 milliliters of absolute benzene. The reaction mixture was then heated for a further hour at 40° C, cooled, and the crystalline product was filtered off with suction and dried.

Yield 24 grams, melting point 111° – 112° C. Analysis:

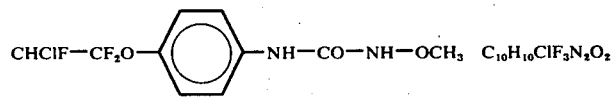

N-[4-(+1',1',2'-trifluoro-2'-chloro-ethoxy)-phenyl]-N'-methyl-methoxyures molecular weight 298.5 calculated 12.0% Cl 9.4% N found 12.3% Cl 9.4% N

EXAMPLE 4

Gaseous dimethylamine was introduced into a solution of 50 grams of 4-(1',1',2'-trifluoro-2'-chloroethoxy)-phenylisocyanate in 100 milliliters of petroleum ether at room temperature and whilst stirring until solution was saturated. The reaction mixture was then maintained for a further hour at 40° C, cooled, the crystalline product was filtered off with suction and recrystallized from n-propanol.

Yield 48 grams, melting point 136° – 138° C Analysis:

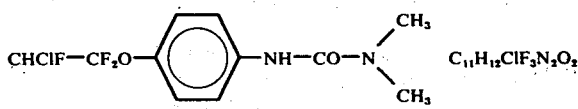

N-[4-(1',1',2'-trifluoro-2'-chloro-ethoxy)-phenyl]-N',N'-dimethylurea molecular weight 296.5 calculated 12.0% Cl 9.4 % N found 12.3 % Cl 9.5 % N

EXAMPLE 5

A solution of 0.2 mole (22 grams) of dimethyl-carbamic acid chloride in 25 milliliters of absolute benzene was dropped at 40° C with stirring into a mixture of 0.2 mole (45 grams) of 4-(1',1',2'-trifluoro-2'-chloro-ethoxy)-aniline, 200 milliliters of absolute benzene and 0.2 mole (20 grams) of triethylamine. The reaction mixture was then heated for a further 2 hours at 40° C. After cooling, the reaction product was filtered off with suction, washed with water until it was free from chlorine and recrystallized twice from n-propanol Yield 38 grams, melting point 135° – 138° C. The mixed melting point with the compound prepared according to Example 4 did not show a depression.

EXAMPLE 6

0.22 mole (14 grams) of O,N-dimethylhydroxylamine was added at room temperature and with stirring to a solution of 0.2 mole (50 grams) of 4-(1',1',2'-trifluoro-2'-chloro-ethoxy)-phenylisocyanate in 100 milliliters of absolute benzene. The reaction mixture was heated for a further hour at 40° C, cooled, and the crystalline product was filtered off with suction and recrystallized from i-propanol.

Yield 49 grams, melting point 89° – 90° C. Analysis:

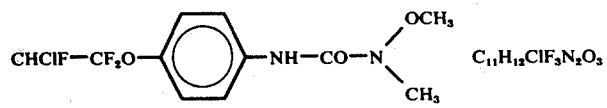

N-[4-(1',1',2'-trifluoro-2'-chloro-ethoxy)-phenyl]-N-methoxy-N'-methylurea molecular weight 312.5
calculated 9.0% N 11.3% Cl found 8.8% N 11.6% Cl

EXAMPLE 7

A solution of 0.2 mole (58 grams) of 4-(1',1',2'-trifluoro-2'-chloro-ethoxy)-phenylcarbamic acid chloride in 100 milliliters of absolute benzene was dropped at 40° C whilst stirring into a mixture of 0.2 mole (12 grams) of O,N-di-methylhydroxylamine, 100 milliliters of absolute benzene and 0.2 mole (20 grams) of triethylamine. The reaction mixture was maintained for a further two hours at 40° C. After cooling the reaction product was filtered off with suction, washed with water until it was free from chlorine and recrystallized from i-propanol Yield 41 grams, melting point 88° – 89° C. The mixed melting point with the compound prepared according to Example 6 did not show a depression.

EXAMPLE 8

200 milliliters of methanol and 20 milliliters of sodium hydroxide solution of 33% strength were added to 0.2 mole (60 grams) of N-[4-(1',1',2'-trifluoro-2'-chloro-ethoxy)phenyl]-N'-methoxyurea prepared according to Example 3. Whilst cooling with ice and stirring, 0.22 mole (28 grams) of dimethylsulfate were dropped into the mixture. After stirring for a further hour at 30° – 35° C an excess of water was added, the precipitated reaction product was filtered off with suction, washed with water and recrystallized from i-propanol. Yield 45 grams, melting point 87° – 89° C. The mixed melting point with the compound prepared according to Example 6 did not show a depression.

EXAMPLE 9

0.2 mole (60 grams) of N-[4-(1',1',2'-trifluoro-2'-chloroethoxy)-phenyl]-N'-methyl-N'-hydroxy-urea, obtained by additive reaction of N-methyl-hydroxylamines with the correspondingly substituted phenylisocyanate, were dissolved in 250 milliliters of methanol. 0.22 mole NaOH (20 milliliters of sodium hydroxide solution of 33% strength) and 0.22 mole (28 grams) of dimethylsulfate were simultaneously added drop by drop whilst stirring at 40° C to the said solution. the mixture was allowed to react for a further hour at 40° C, an excess of ice water was added, the precipitated reaction product was filtered off with suction and recrystallized twice from i-propanol. Yield 38 grams, melting point 86° – 88° C. The mixed melting point with the compound prepared according to Example 6 did not show a depression.

EXAMPLE 10

300 milliliters of methanol were added to 0.2 mole (57 grams) of N-[4-(1',1',2'-trifluoro-2'-chloro-ethoxy)-phenyl]-N'-hydroxy-urea. While vigorously stirring at a pH of 9 – 10 and a temperature of 20° C, 50 milliliters of 10N sodium hydroxide solution and 0.5 mole (63 grams) of dimethyl-sulfate were simultaneously poured into the mixture obtained. In the second half of the reaction the pH rose to 10 – 11. The reaction mixture was maintained for another hour at 20° C, then diluted with an excess of ice water, the precipitated reaction product was filtered off with suction, washed with water and recrystallized twice from i-propanol. Yield 40 grams, melting point 86°– 88° C. The mixed melting point with the compound prepared according to Example 6 did not show a depression.

The compounds listed in the following table were prepared in a manner analogous to that of the example indicated in column 3 with the use of the reactants indicated in column 4.

| Example No. | Final product molecular weight | | reactants | | melting point °C | Analysis calculated | found |
|---|---|---|---|---|---|---|---|
| | | preparations analogous to Example | | | | | |
| 11 | 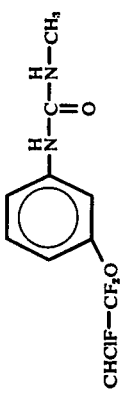 CHClF—CF₂O 282.5 | 1 |  CHClF—CF₂O | CH₃—NH₂ | 90–92 | 9.9 % N 12.6 % Cl | 10.1 % N 12.6 % Cl |
| 12 | 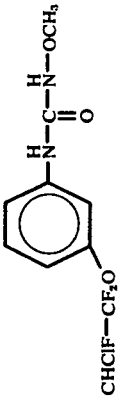 CHClF—CF₂O 298.5 | 3 | 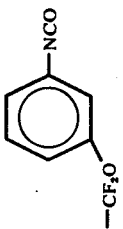 CHClF—CF₂O | H₂N—OCH₃ | 82–83 | 9.4 % N 11.9 % Cl | 9.6 % N 12.0 % Cl |
| 13 | 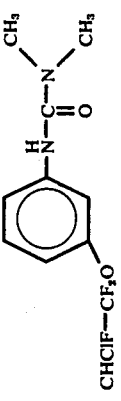 CHClF—CF₂O 296.5 | 4 |  CHClF—CF₂O | CH₃\HN/CH₃ | 118–121 | 9.4 % N 12.0 % Cl | 9.8 % N 12.0 % Cl |
| 14 | 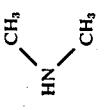 CHClF—CF₂O 312.5 | 10 | 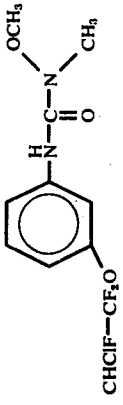 CHClF—CF₂O | H₂N—OH, dimethyl sulfate/NaOH | 79–82 | 9.0 % N 11.3 % Cl | 9.1 % N 11.2 % Cl |
| 15 | 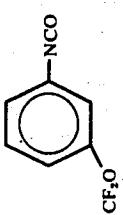 CHClF—CF₂O 340.5 | 6 | 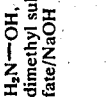 CHClF—CF₂O | OC₂H₅\HN/C₂H₅ | oil | 8.2 % N 10.4 % Cl | 8.1 % N 10.1 % Cl |
| 16 | 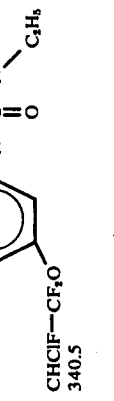 CHClF—CF₂O 296.5 | 2 |  CHClF—CF₂O (with CH₃) | CH₃—NCO | 123–125 | 9.4 % N 12.0 % Cl | 9.4 % N 11.7 % Cl |

-continued

| Example No. | Final product molecular weight | preparations analogous to Example | reactants | | melting point °C | Analysis calculated | Analysis found |
|---|---|---|---|---|---|---|---|
| 17 | CHClF–CF$_2$O–(C$_6$H$_3$(CH$_3$))–NH–C(=O)–N(CH$_3$)$_2$<br>310.5 | 5 | CHClF–CF$_2$O–(C$_6$H$_3$(CH$_3$))–NH$_2$ | H$_3$C–N(CO–Cl)–CH$_3$, Triethylamine | 126–128 | 9.0 % N<br>11.4 % Cl | 8.8 % N<br>11.2 % Cl |
| 18 | CHClF–CF$_2$O–(C$_6$H$_3$(CH$_3$))–NH–C(=O)–N(OCH$_3$)(CH$_3$)<br>326.5 | 6 | CHClF–CF$_2$O–(C$_6$H$_3$(CH$_3$))–NCO | HN(OCH$_3$)(CH$_3$) | 58–60 | 8.6 % N<br>10.9 % Cl | 8.6 % N<br>11.0 % Cl |
| 19 | CHF$_2$–CF$_2$O–C$_6$H$_4$–NH–C(=O)–N(CH$_3$)$_2$<br>280 | 4 | CHF$_2$–CF$_2$O–C$_6$H$_4$–NCO | HN(CH$_3$)(CH$_3$) | 122–123 | 10.0 % N<br>27.1 % F | 10.1 % N<br>27.4 % F |
| 20 | CHF$_2$–CF$_2$O–C$_6$H$_4$–NH–C(=O)–N(OCH$_3$)(CH$_3$)<br>296 | 6 | CHF$_2$–CF$_2$O–C$_6$H$_4$–NCO | HN(OCH$_3$)(CH$_3$) | 67–69 | 9.5 % N<br>25.6 % F | 9.5 % N<br>25.2 % F |
| 21 | CHF$_2$–CF$_2$O–C$_6$H$_4$–NH–C(=O)–NH–CH$_3$<br>266 | 1 | CHF$_2$–CF$_2$O–C$_6$H$_4$–NCO | CH$_3$–NH$_2$ | 96–98 | 10.5 % N<br>28.6 % F | 10.6 % N<br>28.5 % F |
| 22 | CHF$_2$–CF$_2$O–C$_6$H$_4$–NH–C(=O)–N(CH$_3$)$_2$<br>280 | 4 | CHF$_2$–CF$_2$O–C$_6$H$_4$–NCO | HN(CH$_3$)(CH$_3$) | 113–115 | 10.0 % N<br>27.1 % F | 10.2 % N<br>27.0 % F |
| 23 | CHF$_2$–CF$_2$O–C$_6$H$_4$–NH–C(=O)–N(OCH$_3$)(CH$_3$)<br>296 | 10 | CHF$_2$–CF$_2$O–C$_6$H$_4$–NCO | H$_2$N–OH dimethyl sulfate/NaOH | 57–58 | 9.5 % N<br>25.6 % F | 9.7 % N<br>25.7 % F |

| Example No. | Final product molecular weight | preparations analogous to Example | reactants | | melting point °C | Analysis calculated | Analysis found |
|---|---|---|---|---|---|---|---|
| 24 | [structure: CHF₂–CF₂O–phenyl(CH₃)–NH–CO–NH–CH₃] 280 | 1 | [structure: CHF₂–CF₂O–phenyl(CH₃)–NCO] | CH₃–NH–CH₃ | 129–131 | 10.0 % N<br>27.1 % F | 10.5 % N<br>26.7 % F |
| 25 | [structure: CHF₂–CF₂O–phenyl(CH₃)–N(CH₃)–CO–N(CH₃)₂] 294 | 4 | [structure: CHF₂–CF₂O–phenyl(CH₃)–NCO] | CH₃–NH–CH₃ | 124–126 | 9.5 % N<br>25.8 % F | 9.7 % N<br>25.7 % F |
| 26 | [structure: CHF₂–CF₂O–phenyl(CH₃)–N(CH₃)–CO–N(CH₃)₂] 310 | 8 | [structure: CHF₂–CF₂O–phenyl(CH₃)–N(OCH₃)–CO–NH–H] | dimethylsulfate<br>NaOH | 61–63 | 9.0 % N<br>24.5 % F | 9.0 % N<br>23.9 % F |
| 27 | [structure: CF₃–CHF–CF₂O–phenyl–NH–CO–N(CH₃)₂] 330 | 4 | [structure: CF₃–CHF–CF₂O–phenyl–NCO] | CH₃–NH–CH₃ | 107–108 | 8.5 % N<br>34.5 % F | 8.7 % N<br>34.2 % F |
| 28 | [structure: CF₃–CHF–CF₂O–phenyl–NH–CO–N(OCH₃)(CH₃)] 346 | 7 | [structure: CF₃–CHF–CF₂O–phenyl–NH–CO–Cl] | H₂N(OCH₃)(CH₃)<br>triethylamine | 50–52 | 8.1 % N<br>32.9 % F | 8.3 % N<br>33.2 % F |
| 29 | [structure: CF₃–CHF–CF₂O–phenyl(meta)–NH–CO–N(CH₃)₂] 330 | 4 | [structure: CF₃–CHF–CF₂O–phenyl(meta)–NCO] | CH₃–NH–CH₃ | 98–99 | 8.5 % N<br>34.5 % F | 8.2 % N<br>34.3 % F |
| 30 | [structure: CF₃–CHF–CF₂O–phenyl(meta)–NH–CO–N(OCH₃)(CH₃)] 346 | 10 | [structure: CF₃–CHF–CF₂O–phenyl(meta)–NCO] | NH₂OH<br>dimethylsulfate<br>NaOH | 48–49 | 8.1 % N<br>33.0 % F | 8.1 % N<br>32.7 % F |

-continued

| Example No. | Final product molecular weight | preparations analogous to Example | reactants | | melting point °C | Analysis calculated | Analysis found |
|---|---|---|---|---|---|---|---|
| 31 | CF₃—CHF—CF₂O—⌬(CH₃)—NH—C(=O)—N(CH₃)(CH₃)<br>344 | 7 | CF₃—CHF—CF₂O—⌬(CH₃)—NH—CO—Cl | HN(CH₃)(CH₃)<br>triethylamine | 119–120 | 8.1 % N<br>33.2 % F | 8.3 % N<br>32.6 % F |
| 32 | CF₃—CHF—CF₂O—⌬(CH₃)—NH—C(=O)—N(OCH₃)(CH₃)<br>360 | 6 | CF₃—CHF—CF₂O—⌬(CH₃)—NCO | HN(OCH₃)(CH₃) | | 7.8 % N<br>31.7 % F | 8.1 % N<br>31.1 % F |
| 33 | CH₂F—CF₂O—⌬—NH—C(=O)—NH—CH₃<br>248 | 1 | CH₂F—CF₂O—⌬—NCO | H₂N—CH₃ | 99–100 | 11.3 % N<br>23.0 % F | 11.3 % N<br>23.8 % F |
| 34 | CH₂F—CF₂O—⌬—NH—C(=O)—N(CH₃)(CH₃)<br>262 | 4 | CH₂F—CF₂O—⌬—NCO | HN(CH₃)(CH₃) | 126–128 | 10.7 % N<br>21.7 % F | 10.7 % N<br>21.0 % F |
| 35 | CH₂F—CF₂O—⌬—NH—C(=O)—N(OCH₃)(CH₃)<br>278 | 10 | CH₂F—CF₂O—⌬—NCO | NH₂OH<br>dimethylsulfate<br>NaOH | 41–42 | 10.1 % N<br>20.5 % F | 10.4 % N<br>20.0 % F |
| 36 | CHBrF—CF₂O—⌬—NH—C(=O)—N(CH₃)(CH₃)<br>278 | 4 | CHBrF—CF₂O—⌬—NCO | HN(CH₃)(CH₃) | 138–140 | 8.2 % N<br>23.4 % Br | 8.2 % N<br>23.0 % Br |

-continued

| Example No. | Final product molecular weight | preparations analogous to Example | reactants | | melting point °C | Analysis calculated | found |
|---|---|---|---|---|---|---|---|
| 37 | CHBrF—CF₂O-[phenyl]-N(H)-C(=O)-N(CH₃)(OCH₃) 357 | 6 | CHBrF—CF₂O-[phenyl]-NCO | HN(OCH₃)(CH₃) | 80–82 | 7.9 % N 22.4 % Br | 8.0 % N 21.9 % Br |
| 38 | CHBrF—CF₂O-[phenyl]-N(H)-C(=O)-N(H)(CH₃) 327 | 1 | CHBrF—CF₂O-[phenyl]-NCO | CH₃—NH₂ | 89–91 | 8.6 % N 24.4 % F | 8.7 % N 23.9 % F |
| 39 | CHBrF—CF₂O-[phenyl]-N(H)-C(=O)-N(CH₃)(CH₃) 341 | 4 | CHBrF—CF₂O-[phenyl]-NCO | HN(CH₃)(CH₃) | 116–117 | 8.2 % N 23.4 % F | 8.3 % N 23.9 % F |
| 40 | CHBrF—CF₂O-[phenyl]-N(H)-C(=O)-N(OCH₃)(CH₃) 357 | 6 | CHBrF—CF₂O-[phenyl]-NCO | HN(OCH₃)(CH₃) | 88–90 | 7.9 % N 22.4 % F | 8.0 % N 22.4 % F |
| 41 | CHBrF—CF₂O-[phenyl(CH₃)]-N(H)-C(=O)-N(CH₃)(CH₃) 341 | 2 | CHBrF—CF₂O-[phenyl(CH₃)]-NH₂ | CH₃—NCO | 128 | 8.2 % N | 8.4 % N |
| 42 | CHBrF—CF₂O-[phenyl(CH₃)]-N(H)-C(=O)-N(CH₃)(CH₃) 355 | 4 | CHBrF—CF₂O-[phenyl(CH₃)]-NCO | HN(CH₃)(CH₃) | 123–124 | 7.9 % N 22.5 % Br | 8.2 % N 22.8 % Br |
| 43 | CHBrF—CF₂O-[phenyl(CH₃)]-N(H)-C(=O)-N(OCH₃)(CH₃) 355 | 6 | CHBrF—CF₂O-[phenyl(CH₃)]-NCO | HN(OCH₃)(CH₃) | 58 | 7.6 % N 21.6 % Br | 7.7 % N 21.8 % Br |

-continued

| Example No. | Final product molecular weight | preparations analogous to Example | reactants | | melting point °C | Analysis calculated | found |
|---|---|---|---|---|---|---|---|
| 44 | [3-(CF₃-CF₂O)-C₆H₄]-NH-C(=O)-N(CH₃)(CH₃); CF₃—CF₂O 298 | 5 | 3-(CF₃—CF₂O)-C₆H₄-NH₂ | CH₃-N(CH₃)-CO-Cl; triethylamine | 124–126 | 9.4 % N; 31.9 % F | 9.6 % N; 31.8 % F |
| 45 | 4-(Cl₂C=CH-CH₂O)-C₆H₄-NH-C(=O)-NH-CH₃; 275 | 2 | 4-(Cl₂C=CH-CH₂O)-C₆H₄-NH₂ | CH₃—N=C=O | 154–155 | 10.2 % N; 25.8 % Cl | 10.3 % N; 25.6 % Cl |
| 46 | 4-(Cl₂C=CH-CH₂O)-C₆H₄-N(CH₃)-C(=O)-N(CH₃)(CH₃); 289 | 4 | 4-(Cl₂C=CH-CH₂O)-C₆H₄-N=C=O | HN(CH₃)(CH₃) | 103–104 | 9.7 % N; 24.6 % Cl | 9.9 % N; 24.3 % Cl |
| 47 | 4-(Cl₂C=CH-CH₂O)-C₆H₄-N(CH₃)-C(=O)-N(CH₃)(OCH₃); 305 | 6 | 4-(Cl₂C=CH-CH₂O)-C₆H₄-N=C=O | HN(CH₃)(OCH₃) | 81–82 | 9.2 % N; 23.2 % Cl | 8.9 % N; 23.1 % Cl |
| 48 | 4-(HCCl=CCl-O)-C₆H₄-NH-C(=O)-NH-CH₃; 261 | 1 | 4-(HCCl=CCl-O)-C₆H₄-NH₂ | CH₃—N=C=O | 145–146 | 10.7 % N; 27.2 % Cl | 10.9 % N; 27.4 % Cl |
| 49 | 4-(HCCl=CCl-O)-C₆H₄-N(CH₃)-C(=O)-N(CH₃)(CH₃); 275 | 5 | 4-(HCCl=CCl-O)-C₆H₄-NH₂ | Cl-C(=O)-N(CH₃)(CH₃) | 153–155 | 10.2 % N; 25.8 % Cl | 10.1 % N; 25.8 % Cl |
| 50 | 4-(CCl₂=CCl-CH₂O)-C₆H₄-NH-C(=O)-N(CH₃)(CH₃); 323.5 | 4 | 4-(CCl₂=CCl-CH₂O)-C₆H₄-N=C=O | HN(CH₃)(CH₃) | 103–105 | 8.7 % N; 33.0 % Cl | 9.0 % N; 32.5 % Cl |
| 51 | 4-(CCl₂=CCl-CH₂O)-C₆H₄-NH-C(=O)-N(CH₃)(OCH₃); 339.5 | 6 | 4-(CCl₂=CCl-CH₂O)-C₆H₄-N=C=O | HN(CH₃)(OCH₃) | 93–94 | 8.3 % N; 31.4 % Cl | 8.6 % N; 31.2 % Cl |

-continued

| Example No. | Final product molecular weight | preparations analogous to Example | reactants | | melting point °C | Analysis calculated | found |
|---|---|---|---|---|---|---|---|
| 52 | $HCCl_2-CF_2O$-C₆H₄-NH-CO-NH-CH₃ <br> 299 | 2 | $HCCl_2-CF_2O$-C₆H₄-NH₂ | $CH_3-N=C=O$ | 151 | 9.4 % N | 9.4 % N |
| 53 | $HCCl_2-CF_2O$-C₆H₄-NH-CO-N(CH₃)₂ <br> 313 | 4 | $HCCl_2-CF_2O$-C₆H₄-N=C=O | HN(CH₃)₂ | 144–146 | 9.0 % N | 9.2 % N |
| 54 | $HCCl_2-CF_2O$-C₆H₄-NH-CO-N(CH₃)-OCH₃ <br> 315 | 3 | $HCCl_2-CF_2O$-C₆H₄-N=C=O | $H_2N-OCH_3$ | 105 | 8.9 % N | 8.7 % N |
| 55 | $HCCl_2-CF_2O$-C₆H₄-NH-CO-N(CH₃)-OCH₃ <br> 329 | 6 | $HCCl_2-CF_2O$-C₆H₄-N=C=O | HN(CH₃)(OCH₃) | 60 | 8.5 % N | 8.4 % N |
| 56 | $HCCl_2-CF_2O$-C₆H₄-NH-CO-N[C₃H₇(n)]₂ <br> 396 | 4 | $HCCl_2-CF_2O$-C₆H₄-N=C=O | HN[C₃H₇(n)]₂ | 103–105 | 7.6 % N | 7.5 % N |
| 57 | 2-(OCF₂-CCl₂H)-C₆H₄-NH-CO-NH-CH₃ <br> 299 | 2 | 2-(OCF₂-CCl₂H)-C₆H₄-NH₂ | $CH_3-N=C=O$ | 170–173 | 9.4 % N | 9.7 % N |
| 58 | 3-($HCCl_2-CF_2O$)-C₆H₄-NH-CO-NH-CH₃ <br> 299 | 2 | 3-($HCCl_2-CF_2O$)-C₆H₄-NH₂ | $CH_3-N=C=O$ | 104–106 | 9.4 % N | 9.3 % N |

-continued

| Example No. | Final product molecular weight | preparations analogous to Example | reactants | | melting point °C | Analysis calculated | Analysis found |
|---|---|---|---|---|---|---|---|
| 59 | HCCl₂—CF₂O—C₆H₄—NH—C(=O)—N(CH₃)(CH₃)  313 | 4 | HCCl₂—CF₂O—C₆H₄—N=C=O | HN(CH₃)(CH₃) | 125 | 8.9 % N | 9.0 % N |
| 60 | HCCl₂—CF₂O—C₆H₄—NH—C(=O)—NH—OCH₃  315 | 3 | HCCl₂—CF₂O—C₆H₄—N=C=O | H₂N—OCH₃ | 100–102 | 8.9 % N | 8.7 % N |
| 61 | HCCl₂—CF₂O—C₆H₄—N(CH₃)—C(=O)—OCH₃  329 | 6 | HCCl₂—CF₂O—C₆H₄—N=C=O | HN(CH₃)(OCH₃) | 74–76 | 8.5 % N | 8.5 % N |
| 62 | CCl₃—CF₂O—C₆H₄—NH—C(=O)—NH—CH₃  333.5 | 1 | CCl₃—CF₂O—C₆H₄—N=C=O | H₂N—CH₃ | 158–159 | 8.4 % N  31.9 % Cl | 8.7 % N  31.5 % Cl |
| 63 | CCl₃—CF₂O—C₆H₄—NH—C(=O)—N(CH₃)(CH₃)  347.5 | 4 | CCl₃—CF₂O—C₆H₄—N=C=O | HN(CH₃)(CH₃) | 200–201 | 8.1 % N | 8.2 % N |
| 64 | CCl₃—CF₂O—C₆H₄—NH—C(=O)—N(CH₃)(OCH₃)  363.5 | 6 | CCl₃—CF₂O—C₆H₄—N=C=O | HN(CH₃)(OCH₃) | 148–150 | 7.7 % N  29.3 % Cl | 8.0 % N  28.9 % Cl |
| 65 | CCl₃—CF₂O—C₆H₄—NH—C(=O)—N(C₂H₅)(C₂H₅)  375.5 | 4 | CCl₃—CF₂O—C₆H₄—N=C=O | HN(C₂H₅)(C₂H₅) | 155–157 | 7.5 % N | 7.4 % N |

-continued

| Example No. | Final product molecular weight | preparations analogous to Example | reactants | | melting point °C | Analysis calculated | Analysis found |
|---|---|---|---|---|---|---|---|
| 66 | 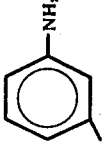<br>261 | 2 | 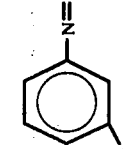 | $CH_3-N\!=\!C\!=\!O$ | 157-159 | 10.7 % N<br>27.2 % Cl | 11.1 % N<br>26.7 % Cl |
| 67 | 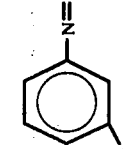<br>275 | 4 | 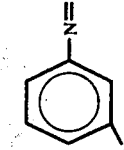 | $\underset{HN}{CH_3}\diagdown\underset{}{CH_3}$ | 105-106 | 10.2 % N<br>25.8 % Cl | 9.9 % N<br>25.2 % Cl |
| 68 | 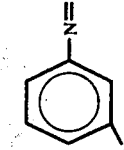<br>291 | 6 | 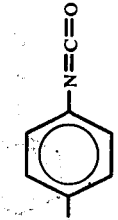 | $\underset{HN}{CH_3}\diagdown\underset{}{OCH_3}$ | 72-73 | 9.6 % N<br>24.4 % Cl | 9.6 % N<br>24.0 % Cl |
| 69 | 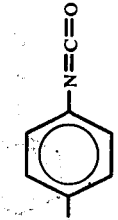<br>277 | 3 | 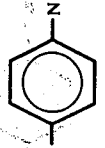 | $H_2N-OCH_3$ | 118-120 | 10.1 % N<br>25.6 % Cl | 10.5 % N<br>25.1 % Cl |
| 70 | 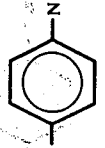<br>291 | 6 | 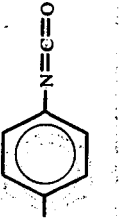 | $\underset{HN}{CH_3}\diagdown\underset{}{OCH_3}$ | 98-101 | 9.6 % N<br>24.4 % Cl | 9.3 % N<br>24.0 % Cl |
| 71 | 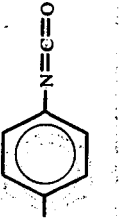<br>303 | 4 |  | $\underset{HN}{C_2H_5}\diagdown\underset{}{C_2H_5}$ | 110-112 | 9.2 % N<br>23.4 % Cl | 8.7 % N<br>23.1 % Cl |
| 72 | <br>359 | 4 | | $\underset{HN}{C_4H_9\,(n)}\diagdown\underset{}{C_4H_9\,(n)}$ | 65-68 | 7.8 % N<br>19.7 % Cl | 7.4 % N<br>19.9 % Cl |

-continued

| Example No. | Final product molecular weight | preparations analogous to Example | reactants | | melting point °C | Analysis calculated | Analysis found |
|---|---|---|---|---|---|---|---|
| 73 | ![structure] NH—C—NH—CH₃, O; CCl₂=CCl—CH₂O | 309.5 | 2 | ![structure] NH₂; CCl₂=CCl—CH₂O | CH₃—N=C=O | 156–158 | 9.1 % N<br>34.4 % Cl | 9.2 % N<br>33.9 % Cl |
| 74 | ![structure] with N(CH₃)₂—C(=O)—NH—; HCBr=CBrO— | 364 | 4 | ![structure] N=C=O; HCBr=CBrO— | CH₃\HN/CH₃ | 158–160 | 7.7 % N<br>43.9 % Br | 8.1 % N<br>44.1 % Br |
| 75 | ![structure] NH—C—NH—CH₃, O; CF₃—C(Cl)=C(O—)CF₃ | 362.5 | 2 | ![structure] NH₂; CF₃—C(Cl)=C(O—)CF₃ | CH₃—N=C=O | 182–184 | 7.2 % N<br>9.8 % Cl | 7.6 % N<br>9.9 % Cl |
| 76 | ![structure] NH—C—NH—CH₃, O; HCCl=CClO— ring-CH₃ | 275 | 2 | ![structure] NH₂; HCCl=CClO— ring-CH₃ | CH₃—N=C=O | 156–158 | 10.2 % N<br>25.8 % Cl | 10.4 % N<br>25.8 % Cl |
| 77 | ![structure] NH—C—N(CH₃)₂, O; HCCl=CClO— ring-CH₃ | 289 | 4 | ![structure] N=C=O; HCCl=CClO— ring-CH₃ | CH₃\HN/CH₃ | 181 | 9.7 % N<br>24.6 % Cl | 9.7 % N<br>24.6 % Cl |
| 78 | ![structure] NH—C—N(CH₃)(OCH₃), O; HCCl=CClO— ring-CH₃ | 305 | 6 | ![structure] N=C=O; HCCl=CClO— ring-CH₃ | CH₃\HN/OCH₃ | 111–113 | 9.2 % N<br>23.2 % Cl | 9.0 % N<br>23.2 % Cl |
| 79 | ![structure] NH—C—N(CH₃)₂, O; HCCl=CClO— ring-CH₃O | 305 | 4 | ![structure] N=C=O; HCCl=CClO— ring-CH₃O | CH₃\HN/CH₃ | 171–173 | 9.2 % N<br>23.2 % Cl | 9.4 % N<br>23.4 % Cl |

-continued

| Example No. | Final product molecular weight | preparations analogous to Example | reactants | | melting point °C | Analysis calculated | Analysis found |
|---|---|---|---|---|---|---|---|
| 80 | 321, structure: phenyl ring with NH-C(=O)-N(CH₃)(OCH₃), 4-HCCl=CClO, 3-CH₃O | 6 | 3-CH₃O, 4-HCCl=CClO phenyl isocyanate | HN(CH₃)(OCH₃) | 85–87 | 8.7 % N<br>22.1 % Cl | 8.9 % N<br>22.1 % Cl |
| 81 | 295.5, structure: phenyl with NH-C(=O)-NH-CH₃, 4-Cl, 3-HCCl=CClO | 2 | 3-HCCl=CClO, 4-Cl aniline | CH₃-N=C=O | 182–186 | 9.5 % N<br>36.0 % Cl | 9.3 % N<br>36.0 % Cl |
| 82 | 309.5, structure: phenyl with NH-C(=O)-N(CH₃)(CH₃), 4-Cl, 3-HCCl=CClO | 4 | 3-HCCl=CClO, 4-Cl phenyl isocyanate | HN(CH₃)(CH₃) | 192–195 | 9.0 % N<br>34.4 % Cl | 9.3 % N<br>33.8 % Cl |
| 83 | —, structure: phenyl with NH-C(=O)-N(CH₃)(OCH₃), 4-Cl, 3-HCCl=CClO | 6 | 3-HCCl=CClO, 4-Cl phenyl isocyanate | HN(CH₃)(OCH₃) | 162–164 | 8.6 % N<br>32.7 % Cl | 8.8 % N<br>32.4 % Cl |
| 84 | 275, structure: phenyl with NH-C(=O)-NH-CH₃, 4-CH₃, 3-HCCl=CClO | 1 | 3-HCCl=CClO, 4-CH₃ phenyl isocyanate | H₂N-CH₃ | 171–173 | 10.2 % N<br>25.8 % Cl | 10.0 % N<br>25.6 % Cl |
| 85 | 289, structure: phenyl with NH-C(=O)-N(CH₃)(CH₃), 4-CH₃, 3-HCCl=CClO | 4 | 3-HCCl=CClO, 4-CH₃ phenyl isocyanate | HN(CH₃)(CH₃) | 192–193 | 9.7 % N<br>24.6 % Cl | 9.9 % N<br>24.6 % Cl |
| 86 | 305, structure: phenyl with NH-C(=O)-N(CH₃)(OCH₃), 4-CH₃, 3-HCCl=CClO | 6 | 3-HCCl=CClO, 4-CH₃ phenyl isocyanate | HN(CH₃)(OCH₃) | 126–129 | 9.2 % N<br>23.3 % Cl | 9.0 % N<br>23.3 % Cl |

-continued

| Example No. | Final product molecular weight | preparations analogous to Example | reactants | | melting point °C | Analysis calculated | found |
|---|---|---|---|---|---|---|---|
| 87 | $HCCl_2-CF_2O$–[phenyl(CH_3)]–NH–CO–NH–CH_3; 313 | 2 | $HCCl_2-CF_2O$–[phenyl(CH_3)]–NH_2 | $CH_3-N=C=O$ | 138 | 8.9 % N | 9.0 % N |
| 88 | $HCCl_2-CF_2O$–[phenyl(CH_3)]–NH–CO–NH–OCH_3; 329 | 3 | $HCCl_2-CF_2O$–[phenyl(CH_3)]–N=C=O | $H_2N-OCH_3$ | 105–106 | 8.5 % N | 8.8 % N |
| 89 | $HCCl_2-CF_2O$–[phenyl(CH_3)]–NH–CO–N(C_2H_5)_2; 355 | 4 | $HCCl_2-CF_2O$–[phenyl(CH_3)]–N=C=O | $HN(C_2H_5)_2$ | 114–115 | 7.9 % N | 7.9 % N |
| 90 | $HCCl_2-CF_2O$–[phenyl(CH_3)]–NH–CO–NH–CH_3; 313 | 2 | $HCCl_2-CF_2O$–[phenyl(CH_3)]–NH_2 | $CH_3-N=C=O$ | 159–161 | 8.9 % N | 9.2 % N |
| 91 | $HCCl_2-CF_2O$–[phenyl(CH_3)]–NH–CO–N(CH_3)_2; 327 | 4 | $HCCl_2-CF_2O$–[phenyl(CH_3)]–N=C=O | $HN(CH_3)_2$ | 95–96 | 8.6 % N; 21.7 % Cl | 8.7 % N; 21.3 % Cl |
| 92 | $HCCl_2-CF_2O$–[phenyl(CH_3)]–NH–CO–N(CH_3)(OCH_3); 343 | 6 | $HCCl_2-CF_2O$–[phenyl(CH_3)]–N=C=O | $HN(CH_3)(OCH_3)$ | 71 | 8.2 % N | 8.2 % N |
| 93 | $HCCl_2-CF_2O$–[phenyl(CH_3)]–NH–CO–N(CH_3)_2; 327 | 4 | $HCCl_2-CF_2O$–[phenyl(CH_3)]–N=C=O | $HN(CH_3)_2$ | 140 | 8.6 % N; 21.7 % Cl | 8.7 % N; 21.7 % Cl |

-continued

| Example No. | Final product molecular weight | preparations analogous to Example | reactants | | melting point °C | Analysis calculated | found |
|---|---|---|---|---|---|---|---|
| 94 | [3-methyl-4-(dichlorofluoromethoxy)phenyl]-N-methyl-N-methoxy urea; MW 343 | 6 | 3-methyl-4-(dichlorofluoromethoxy)phenyl isocyanate | HN(CH₃)(OCH₃) | 79– | 8.2 % N<br>20.7 % Cl | 8.2 % N<br>20.6 % Cl |
| 95 | 313 | 1 | 3-(dichlorofluoromethoxy)-4-methylphenyl isocyanate | H₂N–CH₃ | 162–163 | 8.9 % N | 9.3 % N |
| 96 | 327 | 5 | 3-(dichlorofluoromethoxy)-4-methyl aniline | Cl–C(=O)–N(CH₃)₂ | 117–119 | 8.6 % N<br>21.7 % Cl | 8.7 % N<br>21.6 % Cl |
| 97 | 343 | 6 | 3-(dichlorofluoromethoxy)-4-methylphenyl isocyanate | HN(CH₃)(OCH₃) | 89–91 | 8.2 % N | 8.5 % N |
| 98 | 367 | 1 | 3-methyl-4-(dichlorofluoromethoxy)phenyl isocyanate, CF₃ | H₂N–CH₃ | 138–140 | 7.6 % N | 7.7 % N |
| 99 | 381 | 4 | 3-methyl-4-(dichlorofluoromethoxy)phenyl isocyanate, CF₃ | HN(CH₃)(CF₃) | 167–169 | 7.4 % N | 7.1 % N |
| 100 | 397 | 6 | 3-(trifluoromethyl)-4-(dichlorofluoromethoxy)phenyl isocyanate | HN(CH₃)(OCH₃) | 60–62 | 7.1 % N<br>17.9 % Cl | 7.3 % N<br>17.6 % Cl |

-continued

| Example No. | Final product molecular weight | preparations analogous to Example | reactants | | melting point °C | Analysis calculated | Analysis found |
|---|---|---|---|---|---|---|---|
| 101 | HCCl$_2$—CF$_2$O—⟨C$_6$H$_3$Cl⟩—NH—C(O)—NH—CH$_3$ <br> 333.5 | 1 | HCCl$_2$—CF$_2$O—⟨C$_6$H$_3$Cl⟩—N=C=O | H$_2$N—CH$_3$ | 137–138 | 8.4 % N <br> 32.0 % Cl | 8.3 % N <br> 31.7 % Cl |
| 102 | HCCl$_2$—CF$_2$O—⟨C$_6$H$_3$Cl⟩—NH—C(O)—NH—OCH$_3$ <br> 349.5 | 3 | HCCl$_2$—CF$_2$O—⟨C$_6$H$_3$Cl⟩—N=C=O | H$_2$N—OCH$_3$ | 118 | 8.0 % N <br> 30.4 % Cl | 8.1 % N <br> 29.9 % Cl |
| 103 | HCCl$_2$—CF$_2$O—⟨C$_6$H$_3$Cl⟩—NH—C(O)—N(CH$_3$)$_2$ <br> 347.5 | 4 | HCCl$_2$—CF$_2$O—⟨C$_6$H$_3$Cl⟩—N=C=O | HN(CH$_3$)$_2$ | 145 | 8.1 % N <br> 30.6 % Cl | 8.2 % N <br> 30.2 % Cl |
| 104 | HCCl$_2$—CF$_2$O—⟨C$_6$H$_3$Cl⟩—NH—C(O)—N(CH$_3$)(OCH$_3$) <br> 363.5 | 6 | HCCl$_2$—CF$_2$O—⟨C$_6$H$_3$Cl⟩—N=C=O | HN(CH$_3$)(OCH$_3$) | 92–93 | 7.7 % N <br> 29.3 % Cl | 8.0 % N <br> 29.2 % Cl |
| 105 | HCCl$_2$—CF$_2$O—⟨C$_6$H$_3$Cl⟩—NH—C(O)—NH—CH$_3$ <br> 333.5 | N | HCCl$_2$—CF$_2$O—⟨C$_6$H$_3$Cl⟩—N=C=O | H$_2$N—CH$_3$ | 156–158 | 8.4 % N <br> 32.0 % Cl | 8.6 % N <br> 31.8 % Cl |
| 106 | HCCl$_2$—CF$_2$O—⟨C$_6$H$_3$Cl⟩—NH—C(O)—N(CH$_3$)$_2$ <br> 347.5 | 4 | HCCl$_2$—CF$_2$O—⟨C$_6$H$_3$Cl⟩—N=C=O | HN(CH$_3$)$_2$ | 92–94 | 8.1 % N | 8.0 % N |
| 107 | HCCl$_2$—CF$_2$O—⟨C$_6$H$_3$Cl⟩—NH—C(O)—N(CH$_3$)(OCH$_3$) <br> 363.5 | 6 | HCCl$_2$—CF$_2$O—⟨C$_6$H$_3$Cl⟩—N=C=O | HN(CH$_3$)(OCH$_3$) | 54–55 | 7.7 % N | 7.9 % N |

-continued

| Example No. | Final product molecular weight | preparations analogous to Example | reactants | | melting point °C | Analysis calculated | found |
|---|---|---|---|---|---|---|---|
| 108 | 4-Cl, 3-OCF$_2$CHCl$_2$-C$_6$H$_3$-NH-CO-NH-CH$_3$; 333.5 | 1 | 4-Cl, 3-OCF$_2$CHCl$_2$-C$_6$H$_3$-N=C=O | H$_2$N—CH$_3$ | 137–139 | 8.4 % N 32.0 % Cl | 8.6 % N 31.6 % Cl |
| 109 | 4-Cl, 3-OCF$_2$CHCl$_2$-C$_6$H$_3$-NH-CO-N(CH$_3$)$_2$; 347.5 | 4 | 4-Cl, 3-OCF$_2$CHCl$_2$-C$_6$H$_3$-N=C=O | HN(CH$_3$)$_2$ | 115–118 | 8.1 % N | 8.2 % N |
| 110 | 4-Cl, 3-OCF$_2$CHCl$_2$-C$_6$H$_3$-NH-CO-N(CH$_3$)(OCH$_3$); 375.5 | 6 | 4-Cl, 3-OCF$_2$CHCl$_2$-C$_6$H$_3$-N=C=O | CH$_3$-NH-OCH$_3$ | 96–98 | 7.7 % N | 7.8 % N |
| 111 | 4-Cl, 3-OCF$_2$CHCl$_2$-C$_6$H$_3$-NH-CO-N(C$_2$H$_5$)$_2$; 375.5 | 4 | 4-Cl, 3-OCF$_2$CHCl$_2$-C$_6$H$_3$-N=C=O | HN(C$_2$H$_5$)$_2$ | 74–76 | 7.5 % N | 7.5 % N |
| 112 | 4-Br, 3-OCF$_2$CHCl$_2$-C$_6$H$_3$-NH-CO-NH-CH$_3$; 378 | 1 | 4-Br, 3-OCF$_2$CHCl$_2$-C$_6$H$_3$-N=C=O | H$_2$N—CH$_3$ | 157–158 | 7.5 % N 21.2 % Br | 7.8 % N 20.9 % Br |
| 113 | 4-Br, 3-OCF$_2$CHCl$_2$-C$_6$H$_3$-NH-CO-N(CH$_3$)$_2$; 392 | 4 | 4-Br, 3-OCF$_2$CHCl$_2$-C$_6$H$_3$-N=C=O | HN(CH$_3$)$_2$ | 112 | 7.2 % N | 7.4 % N |

-continued

| Example No. | Final product molecular weight | preparations analogous to Example | reactants | | melting point °C | Analysis calculated | found |
|---|---|---|---|---|---|---|---|
| 114 | $HCCl_2-CF_2O$-[phenyl with Br]-NH-C(=O)-N(CH$_3$)(OCH$_3$); 408 | 6 | $HCCl_2-CF_2O$-[phenyl with Br]-N=C=O | HN(CH$_3$)(OCH$_3$) | 94–97 | 6.9 % N | 7.2 % N |
| 115 | $HCCl_2-CF_2O$-[phenyl with Br]-NH-C(=O)-N(C$_2$H$_5$)(C$_2$H$_5$); 420 | 4 | $HCCl_2-CF_2O$-[phenyl with Br]-N=C=O | HN(C$_2$H$_5$)(C$_2$H$_5$) | 105–106 | 6.7 % N | 6.7 % n |
| 116 | $HCCl_2-CF_2O$-[phenyl with OCH$_3$]-NH-C(=O)-NH-CH$_3$; 329 | 2 | $HCCl_2-CF_2O$-[phenyl with OCH$_3$]-NH$_2$ | CH$_3$-N=C=O | 149 | 8.5 % N | 8.6 % N |
| 117 | $HCCl_2-CF_2O$-[phenyl with OCH$_3$]-NH-C(=O)-N(CH$_3$)(CH$_3$); 343 | 4 | $HCCl_2-CF_2O$-[phenyl with OCH$_3$]-N=C=O | HN(CH$_3$)(CH$_3$) | 159 | 8.2 % N | 8.4 % N |
| 118 | $HCCl_2-CF_2O$-[phenyl with OCH$_3$]-NH-C(=O)-N(CH$_3$)(OCH$_3$); 359 | 6 | $HCCl_2-CF_2O$-[phenyl with OCH$_3$]-N=C=O | HN(CH$_3$)(OCH$_3$) | 92–93 | 7.8 % N | 8.0 % n |
| 119 | $HCCl_2-CF_2O$-[phenyl with CH$_3$ and Cl]-NH-C(=O)-NH-CH$_3$; 347.5 | 1 | $HCCl_2-CF_2O$-[phenyl with CH$_3$ and Cl]-N=C=O | H$_2$N-CH$_3$ | 168 | 8.1 % N / 30.7 % Cl | 8.3 % N / 31.3 % Cl |

-continued

| Example No. | Final product molecular weight | preparations analogous to Example | reactants | | melting point °C | Analysis calculated | found |
|---|---|---|---|---|---|---|---|
| 120 | [3-Cl, 4-(HCCl₂-CF₂O), 5-CH₃-phenyl]-NH-C(=O)-N(CH₃)(CH₃); 360.5 | 4 | 3-Cl, 4-(HCCl₂-CF₂O), 5-CH₃-phenyl-N=C=O | HN(CH₃)(CH₃) | 145–147 | 7.8 % N 29.6 % Cl | 7.6 % N 29.4 % Cl |
| 121 | [3-Cl, 4-(HCCl₂-CF₂O), 5-CH₃-phenyl]-NH-C(=O)-N(CH₃)(OCH₃); 377.5 | 6 | 3-Cl, 4-(HCCl₂-CF₂O), 5-CH₃-phenyl-N=C=O | HN(CH₃)(OCH₃) | 105 | 7.6 % N 28.2 % Cl | 7.6 % N 27.9 % Cl |
| 122 | [4-(HCCl₂-CF₂O)-phenyl]-NH-C(=O)-NH-CH₃; 448 | 1 | 4-(HCCl₂-CF₂O)-phenyl-N=C=O | H₂N-CH₃ | 136 | 6.3 % N | 6.6 % N |
| 123 | [3-(HCCl₂-CF₂O)-phenyl]-NH-C(=O)-N(CH₃)(CH₃); 462 | 4 | 3-(HCCl₂-CF₂O)-phenyl-N=C=O | HN(CH₃)(CH₃) | 128–130 | 6.1 % N | 6.2 % N |
| 124 | [3-(HCCl₂-CF₂O)-phenyl]-NH-C(=O)-N(CH₃)(OCH₃); 478 | 6 | 3-(HCCl₂-CF₂O)-phenyl-N=C=O | HN(CH₃)(OCH₃) | 69–70 | 5.9 % N 29.7 % Cl | 6.0 % N 29.3 % Cl |
| 125 | [3-(HCCl₂-CF₂O)-phenyl]-NH-C(=O)-N(C₂H₅)(C₂H₅); 490 | 4 | 3-(HCCl₂-CF₂O)-phenyl-N=C=O | HN(C₂H₅)(C₂H₅) | 51–53 | 5.7 % N | 5.7 % N |

| Example No. | Final product molecular weight | preparations analogous to Example | reactants | | melting point °C | Analysis calculated | found |
|---|---|---|---|---|---|---|---|
| 126 | [structure with cyclopentene-F2,F2,F2,Cl,O-phenyl-NH-C(=O)-NH-CH3] 374.5 | 2 | [4-aminophenoxy-chlorotetrafluorocyclopentene] | CH3—N=C=O | 142–144 | 7.5 % N 9.5 % Cl | 7.3 % N 8.9 % Cl |
| 127 | [structure ...N(CH3)-C(=O)-N(CH3)2] 388.5 | 4 | [4-isocyanatophenoxy-chlorotetrafluorocyclopentene] | CH3\HN/CH3 | 130–132 | 7.2 % N 9.2 % Cl | 7.3 % N 9.4 % Cl |
| 128 | [structure ...NH-C(=O)-N(CH3)(OCH3)] 404.5 | 6 | [4-isocyanatophenoxy-chlorotetrafluorocyclopentene] | CH3\HN/OCH3 | 78–80 | 6.9 % N 8.6 % Cl | 6.9 % N 8.7 % Cl |
| 129 | [structure cyclobutene ...NH-C(=O)-NH-CH3] 324.5 | 2 | [4-aminophenoxy-chlorodifluorocyclobutene] | CH3—N=C=O | 150–151 | 8.6 % N | 8.5 % N |
| 130 | [structure cyclobutene ...N(CH3)-C(=O)-(OCH3)] 354.5 | 6 | [4-isocyanatophenoxy-chlorodifluorocyclobutene] | CH3\HN/OCH3 | 94–97 | 7.9 % N 10.0 % Cl | 7.9 % N 10.0 % Cl |

-continued

| Example No. | Final product molecular weight | preparations analogous to Example | reactants | | melting point °C | Analysis calculated | Analysis found |
|---|---|---|---|---|---|---|---|
| 131 | ClCH₂—CH₂O—C₆H₄—NH—C(=O)—NH—CH₃<br>228.5 | 1 | ClCH₂—CH₂O—C₆H₄—N=C=O | H₂N—CH₃ | 164–166 | 12.3 % N | 12.1 % N |
| 132 | ClCH₂—CH₂O—C₆H₄—NH—C(=O)—N(CH₃)₂<br>242.5 | 4 | ClCH₂—CH₂O—C₆H₄—N=C=O | HN(CH₃)₂ | 104–106 | 11.5 % N<br>14.6 % Cl | 11.8 % N<br>15.2 % Cl |
| 133 | ClCH₂—CH₂O—C₆H₄—NH—C(=O)—N(CH₃)(OCH₃)<br>258.5 | 6 | ClCH₂—CH₂O—C₆H₄—N=C=O | CH₃—HN—OCH₃ | 91–92 | 10.8 % N | 11.1 % N |
| 134 | ClCH₂—CH₂O—C₆H₄(m)—NH—C(=O)—NH—CH₃<br>228.5 | 1 | ClCH₂—CH₂O—C₆H₄(m)—N=C=O | H₂N—CH₃ | 121 | 12.3 % N | 12.4 % N |
| 135 | ClCH₂—CH₂O—C₆H₄(m)—NH—C(=O)—N(CH₃)₂<br>242.5 | 4 | ClCH₂—CH₂O—C₆H₄(m)—N=C=O | HN(CH₃)₂ | 195 | 11.5 % N<br>14.6 % Cl | 11.4 % N<br>14.4 % Cl |
| 136 | ClCH₂—CH₂O—C₆H₄(m)—NH—C(=O)—N(CH₃)(OCH₃)<br>258.5 | 6 | ClCH₂—CH₂O—C₆H₄(m)—N=C=O | CH₃—HN—OCH₃ | 122 | 10.8 % N | 11.0 % N |
| 137 | ClCH₂—CH₂O—C₆H₃(Cl)—NH—C(=O)—NH—CH₃<br>263 | 1 | ClCH₂—CH₂O—C₆H₃(Cl)—N=C=O | H₂N—CH₃ | 102–105 | 10.6 % N | 10.3 % N |

| Example No. | Final product molecular weight | preparations analogous to Example | reactants | | melting point °C | Analysis calculated | found |
|---|---|---|---|---|---|---|---|
| 138 | 4-chloro-phenoxyethyl-NH-C(=O)-N(CH₃)₂ structure; ClCH₂—CH₂O—C₆H₃(Cl)—NH—C(O)—N(CH₃)₂; 277 | 4 | ClCH₂—CH₂O—C₆H₃(Cl)—N=C=O | HN(CH₃)₂ | 123–125 | 10.1 % N / 25.6 % Cl | 10.2 % N / 25.8 % Cl |
| 139 | ClCH₂—CH₂O—C₆H₃(Cl)—NH—C(O)—NH—OCH₃; 279 | 3 | ClCH₂—CH₂O—C₆H₃(Cl)—N=C=O | H₂N—OCH₃ | 130–131 | 10.0 % N / 25.4 % Cl | 10.1 % N / 25.3 % Cl |
| 140 | ClCH₂—CH₂O—C₆H₃(Cl)—NH—C(O)—N(CH₃)(OCH₃); 293 | 6 | ClCH₂—CH₂O—C₆H₃(Cl)—N=C=O | HN(CH₃)(OCH₃) | 112–114 | 9.6 % N | 9.6 % N |
| 141 | ClCH₂—CH₂O—C₆H₃(Cl)—NH—C(O)—NH—CH₃; 263 | 2 | ClCH₂—CH₂O—C₆H₃(Cl)—NH₂ | CH₃—N=C=O | 154–155 | 10.6 % N | 10.6 % N |
| 142 | ClCH₂—CH₂O—C₆H₃(Cl)—NH—C(O)—N(CH₃)₂; 277 | 4 | ClCH₂—CH₂O—C₆H₃(Cl)—N=C=O | HN(CH₃)₂ | 178–179 | 10.1 % N / 25.6 % Cl | 9.9 % N / 25.4 % Cl |
| 143 | ClCH₂—CH₂O—C₆H₃(Cl)—NH—C(O)—N(CH₃)(OCH₃); 293 | 8 | ClCH₂—CH₂O—C₆H₃(Cl)—N=C=O | H₂N—OCH₃ dimethylsulfate | 106–108 | 9.6 % N | 9.3 % N |
| 144 | ClCH₂—CH₂O—C₆H₃(CF₃)—NH—C(O)—N(CH₃)₂; 310.5 | 4 | ClCH₂—CH₂O—C₆H₃(CF₃)—N=C=O | HN(CH₃)₂ | 112–114 | 9.0 % N / 11.4 % Cl | 9.1 % N / 11.6 % Cl |

-continued

| Example No. | Final product molecular weight | preparations analogous to Example | reactants | | melting point °C | Analysis calculated | found |
|---|---|---|---|---|---|---|---|
| 145 | ClCH₂—CH₂O-[3-CF₃-phenyl]-NH-C(=O)-N(CH₃)(OCH₃) <br> 326.5 | 10 | ClCH₂—CH₂O-[3-CF₃-phenyl]-N=C=O | NH₂OH dimethylsulfate | 108–109 | 8.6 % N | 8.6 % N |
| 146 | ClCH₂—CH₂O-[4-CH₃-phenyl]-NH-C(=O)-N(CH₃)(CH₃) <br> 256.5 | 5 | ClCH₂—CH₂O-[4-CH₃-phenyl]-NH₂ | Cl-C(=O)-N(CH₃)(CH₃) | 177–179 | 10.9 % N <br> 13.8 % Cl | 10.9 % N <br> 14.2 % Cl |
| 147 | ClCH₂—CH₂O-[4-CH₃-phenyl]-NH-C(=O)-N(CH₃)(OCH₃) <br> 272.5 | 6 | ClCH₂—CH₂O-[4-CH₃-phenyl]-N=C=O | HN(CH₃)(OCH₃) | 66–68 | 10.3 % N | 10.3 % N |
| 148 | ClCH₂—CH₂O-[4-CH₃-phenyl]-NH-C(=O)-N(CH₃)(OCH₃) <br> 256.5 | 4 | ClCH₂—CH₂O-[4-CH₃-phenyl]-N=C=O | HN(CH₃)(CH₃) | 116–118 | 10.9 % N <br> 13.8 % Cl | 10.9 % N <br> 14.1 % Cl |
| 149 | ClCH₂—CH₂O-[4-CH₃-phenyl]-NH-C(=O)-N(CH₃)(OCH₃) <br> 272.5 | 10 | ClCH₂—CH₂O-[4-CH₃-phenyl]-N=C=O | NH₂OH dimethylsulfate | 64–66 | 10.3 % N <br> 13.0 % Cl | 10.1 % N <br> 13.3 % Cl |
| 150 | HCCl₂—CF₂O-[4-C₂H₅-phenyl]-NH-C(=O)-NH-CH₃ <br> 327 | 2 | HCCl₂—CF₂O-[4-C₂H₅-phenyl]-NH₂ | CH₃—N=C=O | 120–122 | 8.6 % N | 8.8 % Cl |
| 151 | HCCl₂—CF₂O-[4-C₂H₅-phenyl]-NH-C(=O)-N(CH₃)(CH₃) <br> 341 | 4 | HCCl₂—CF₂O-[4-C₂H₅-phenyl]-N=C=O | HN(CH₃)(CH₃) | 159–162 | 8.2 % N <br> 20.8 % Cl | 8.5 % N <br> 20.8 % Cl |

-continued

| Example No. | Final product molecular weight | preparations analogous to Example | reactants | | melting point °C | Analysis calculated | Analysis found |
|---|---|---|---|---|---|---|---|
| 152 | $HCCl_2-CF_2O$—[phenyl with $C_2H_5$]—NH—C(=O)—N(CH$_3$)(OCH$_3$)<br>357 | 6 | $HCCl_2-CF_2O$—[phenyl with $C_2H_5$]—N=C=O | HN(CH$_3$)(OCH$_3$) | 58–60 | 7.9 % N<br>19.9 % Cl | 8.1 % N<br>19.5 % Cl |
| 153 | $HCCl_2-CF_2O$—[phenyl with CH$_3$, CH(CH$_3$)$_2$]—NH—C(=O)—N(CH$_3$)(CH$_3$)<br>369 | 4 | $HCCl_2-CF_2O$—[phenyl with CH$_3$, CH(CH$_3$)$_2$]—N=C=O | HN(CH$_3$)(CH$_3$) | 174–175 | 7.6 % N<br>19.2 % Cl | 7.7 % N<br>18.9 % Cl |
| 154 | $HCCl_2-CF_2O$—[phenyl with CH$_3$, CH(CH$_3$)$_2$]—NH—C(=O)—N(CH$_3$)(OCH$_3$)<br>385 | 6 | $HCCl_2-CF_2O$—[phenyl with CH$_3$, CH(CH$_3$)$_2$]—N=C=O | HN(CH$_3$)(OCH$_3$) | 61–63 | 7.3 % N | 7.5 % N |

EXAMPLE 155

A wettable powder which is easy to disperse in water was obtained by mixing 80 parts by weight of N-[3-(1',-1',2',3',3',3'-hexafluoropropoxy)-phenyl]-N'-, N'-dimethylurea as active ingredient, 17 parts by weight of precipitated silicic acid as inert substance and 3 parts by weight of sodium oleylmethyltaurine as wetting and dispersing agent, and grinding the mixture in a disk attrition mill.

EXAMPLE 156

A dusting powder having good herbicidal properties was obtained by mixing 10 parts by weight of N-[3-methyl-4-(1',1', 2',2'-tetrafluoroethoxy)-phenyl]-N'-methyl-N'-methoxyurea as active ingredient and 90 parts by weight of talc as inert substance and comminuting the mixture in a cross beater mill.

EXAMPLE 157

An emulsion concentrate was obtained from 15 parts by weight of N-[3-(1',1',2'-trifluoro-2'-chloro-ethoxy)-phenyl]-N',N'-dimethylurea, 75 parts by weight of cyclohexanone as solvent and 10 parts of nonylphenol·10 AeO as emulsifier.

The following comparative examples serve to illustrate the invention but they are not intended to limit it thereto.

COMPARATIVE EXAMPLE 1

| In a greenouse the following weeds | |
|---|---|
| wild mustard | Sinapis arvensis |
| chickweed | Stellaria media |
| field camomile | Anthemis arvensis |
| barnyard grass | Echinochloa crus-galli |
| annual meadow grass | Poa annua |
| and maize and cotton (Gossypium sp.) were sown. | |

The surface of the soil was srayed with the following compounds of the invention in the form of wettable powders suspended in water:

I  N-[3-(1',1',2'-trifluoro-2'-chloro-ethoxy)-phenyl]-N-methyl-urea (cf. Example 11)
II  N-[3-(1',1',2'-trifluoro-2'-chloro-ethoxy)-phenyl]-N'-methyl-N'-methoxy-urea (cf. Example 14)
III  N-[3-(1',1',2'-trifluoro-2'-chloro-ethoxy)-phenyl]-N',N'-dimethyl urea (cf. Example 13).

As comparative substance the known urea herbicide N-(3-chloro-4-methoxyphenyl)-N'-methyl-N'-methoxy-urea IV (cf. U.S. Pat. No. 3,228,762) was used.

The evaluation after 6 weeks with concentrations of 0.6 and 1.2 kilograms of active ingredient per hectare gave the followig result:

| | Degree of Damage in percent | | | | | | | |
|---|---|---|---|---|---|---|---|---|
| | I | | II | | III | | IV | |
| | 0.6 | 1.2 | 0.6 | 1.2 | 0.6 | 1.2 | 0.6 | 1.2 |
| weeds (average of 5 types) | 75 | 90 | 93 | 99 | 98 | 100 | 76 | 86 |
| maize | 0 | 0 | 0 | 0 | 10 | 20 | 30 | 50 |
| cotton | 0 | 0 | 0 | 0 | 0 | 0 | 60 | 100 |

The herbicidal effect of substance I of the invention was approximately equal to tht of the known comparative compound IV, whereas substances II and III were distinctly superior. Moreover, the novel compounds did almost no harm to the cultivated plants maize and cotton, which were strongly injured and partly destroyed by the comparative compound IV.

With regard to the herbicidal effect and the damage to the specified cultivated plants the following compounds a. had an effect similar to that of compound I above
N-[3-methyl-4-(1',1',2',2'-tetrafluoro-ethoxy)-phenyl]-N'-methylurea (cf. Example 24)
N-[3-(1',1',2'-trifluoro-2'-bromo-ethoxy)-phenyl]-N',N'-dimethylurea (cf. Example 39)
N-[3-(1',1',2'-trifluoro-2'-bromo-ethoxy)-phenyl]-N'-methylurea (cf. Example 38)
N-[3-(1',1',2'-trifluoro-2'-bromo-ethoxy)-phenyl]-N'-methyl-N'-methoxyurea (cf. Example 40)
N-[4-(1',1',2',2'-tetrafluoro-ethoxy)-phenyl]-N',N'-dimethylurea (cf. Example 19)
N-[3-(1',1',2'-trifluoro-ethoxy)-phenyl]-N'-methylurea (cf. Example 33)

b. had an effect similar to that of compound II above
N-[3-(1',1',2',2'-tetrafluoro-ethoxy)-phenyl]-N'-methyl-urea (cf. Example 21)
N-[3-methyl-4-(1',1',2',2'-tetrafluoro-ethoxy)-phenyl]-N'-methyl-N'-methoxyurea (cf. Example 26)
N-[3-(1',1',2',3',3',3'-hexafluoro-propoxy)-phenyl]-N',N'-dimethylurea (cf. Example 29)
N-[3-(1',1',2'-trifluoro-ethoxy)-phenyl]-N'-methyl-N'-methoxyurea (cf. Example 35)

c. had an effect similar to that of compound III above
N-[3-(1',1',2',2'-tetrafluoro-ethoxy)-phenyl]-N'-methyl-N'-methoxyurea (cf. Example 23)
N-[3-methyl-4-(1',1',2',2'-tetrafluoro-ethoxy)-phenyl]-N'-N'N'-dimethylurea (cf. Example 25)
N-[3-(1',1',2'-trifluoro-ethoxy)-phenyl]-N',N'-dimethylurea (cf. Example 34)

COMPARATIVE EXAMPLE 2

At the same time as the test described above, a comparative test was carried out with horse beans, soybeans (Glycine soya), kidney beans (Phaseolus vulgaris) and maize and the aforesaid weeds, in which test compounds
V  N-[3-(1',1',2',3',3',3'-hexafluoro-propoxy)-phenyl]-N'-methyl-N'-methoxyurea (cf. Example 30) and
VI  N-[4-(1',1',2',3',3',3'-hexafluoro-propoxy)-phenyl]-N',N'-dimethylurea (cf. Example 28)
were compared with comparative compound
IV  N-(3-chloro-4-methoxyphenyl)-N'-methyl-N'-methoxyurea.

The evaluation after 6 weeks gave the following result (concentrations 0.6 and 1.2 kilograms of active ingredient per hectare).

| | Degree of damage in percent | | | | | |
|---|---|---|---|---|---|---|
| | V | | VI | | IV | |
| | 0.6 | 1.1 | 0.6 | 1.2 | 0.6 | 1.2 |
| weeds (average of 5 types) | 90 | 93 | 82 | 88 | 76 | 86 |
| maize | 0 | 0 | 0 | 0 | 30 | 50 |
| soybean | 0 | 0 | 0 | 0 | 40 | 95 |
| horse bean | 0 | 10 | 0 | 0 | 30 | 65 |

-continued

| | Degree of damage in percent | | | | | |
|---|---|---|---|---|---|---|
| | V | | VI | | IV | |
| | 0.6 | 1.1 | 0.6 | 1.2 | 0.6 | 1.2 |
| kidney bean | 0 | 10 | 0 | 0 | 20 | 50 |

With an approximately equal or slightly superior herbicidal effect the novel compounds V and VI did no harm to the 4 types of cultivated plants, which were strongly damaged by comparative compound IV.

COMPARATIVE EXAMPLE 3

In a further test compound VII N-[3-(1',1',2',2'-tetrafluoro-ethoxy)-phenyl]-N',N'-dimethylurea (cf. Example 22) was sprayed in the form of an aqueous suspension on the surface of a soil into which the weeds wild mustard, field camoile, barnyard grass, annual meadow grass and pigweed (*Amaranthus retroflexus*) had been sown together with cotton.

As comparative compound the known urea product metobromuron VIII N-(4-bromophenyl)-N'-methyl-N'-methoxyurea, was used. The result is indicated in the following table. The compounds were used in concentrations of 0.3, 0.6 and 1.2 kilograms per hectare.

| | Degree of damage in percent | | | | | |
|---|---|---|---|---|---|---|
| | VII | | | VIII | | |
| | 0.3 | 0.6 | 1.2 | 0.3 | 0.6 | 1.2 |
| weeds (average of 5 types | 96 | 98 | 100 | 75 | 87 | 94 |
| cotton | 0 | 0 | 0 | 35 | 40 | 75 |

Compound VII of the invention had a distinctly better herbicidal effect than comparative compound VIII and did no harm at all to the cotton which was considerably damaged by metobromuron.

COMPARATIVE EXAMPLE 4

Seeds of cotton (*Gossypium sp.*) and various weeds were sown in pots. On the same day wettable powder formulae suspended in water of the preparations I = N-3-(1',1',2'-trifluoroethoxy)-phenyl-N',N'-dimethylurea (cf. Example 34)

II = N-3-(1',1',2'-trifluoroethoxy)-phenyl-N'-methyl-N'-methoxyurea (cf. Example 35)

III = N-3-(1',1',2'-trifluoroethoxy)-phenyl-N'-methylurea (cf. Example 33)

were sprayed onto the surface of the soil. As comparative substance the preparation of fluometuron (N-3-trifluoro-methyl-phenyl-N',N'-dimethylurea) was used.

An evaluation 5 weeks after the treatment revealed that cotton was not damaged in any place with amounts of 0.3 and 0.6 kilogram of active ingredient per hectare. With respect to the weeds *Sinapis arvensis*, *Amaranthus retroflexus*, *Kochia scoparia* and *Chenopodium album*, the effect of the substances in accordance with the invention was about as good as the effect of the comparative substances, i.e. the weeds mentioned above were completely killed everywhere with 0.3 and 0.6 kilogram per hectare. With respect to some other weeds, however, differences were to be seen, which is shown in the following survey.

| Effect on the weeds, expressed as "degree of damage in %" | | | |
|---|---|---|---|
| | | Effect with | |
| Species of plant | Preparation | 0.3 | 0.6 kg/ha |
| *Ipomoea purpurea* | I | 100 | 100 |
| | II | 100 | 100 |
| | III | 100 | 100 |
| | fluometuron | 85 | 85 |
| *Datura stramonium* | I | 75 | 100 |
| | II | 70 | 100 |
| | III | 80 | 95 |
| | fluometuron | 30 | 60 |
| *Eleusine indica* | I | 100 | 100 |
| | II | 95 | 100 |
| | III | 95 | 100 |
| | fluometuron | 60 | 85 |
| *Setaria viridis* | I | 100 | 100 |
| | II | 95 | 100 |
| | III | 80 | 100 |
| | fluometuron | 65 | 85 |

These values show that the preparations in accordance with the invention have a far better effect on the species of weeds mentioned above than the comparative substance.

COMPARATIVE EXAMPLE 5

In a greenhouse wild mustard and oat were sown in pots. On the day of sowing the soil was treated with a 25 % suspension in water of wettable powders of N-[4-(1',1'-difluoro-2', 2'-dichloroethoxy)-phenyl]-N-methylurea and N-[4-(1',1'-di-fluoro-2',2'-dichloroethoxy)-phenyl]-N',N'-dimethylurea, respectively.

As comparative substance the known urea herbicide N-(4-chlorophenyl)-N'-methyl-N'-isobutinylurea was used.

The test results are indicated in Table I. In the table are given the amount of active ingredient in kilograms per hectare and the effect of the preparation in "degrees of damage"; 100 means total destruction whereas 0 indicates that the plant was not at all damaged. The figures defined the damage in percent.

An evaluation 6 weeks after the treatment exhibited that in concentrations that are destructive to wild mustard the novel compounds do oat very little harm only. With a 100% destruction of the wild mustard the oat was damaged to a degree of 10% only. The corresponding value of the comparative substance amounted to a 75% destruction of the oats. With a degree of damage of the weed of 70–80%, which is fully satisfactory in practice, the oat was still damaged to about 50% by the comparative substance, whereas the novel compounds were fully safe. On the other hand the application of double the amount of the herbicidal agent, which is possible in practice at any time, for example with overlapping spray zones on the field, did not noticeably increase the damage of the oats whereas with the comparative substance the damage rose at once to 90%. Hence, it follows that the application of the novel preparations is much safer.

TABLE 1

| Preparation containing | Test plant | Damage with kilograms of active ingredient per hectare | | | | |
|---|---|---|---|---|---|---|
| | | 10 kg/ha | 5 kg/ha | 2.5 kg/ha | 1.2 kg/ha | 0.6 kg/ha |
| N-[4-(1',1'-difluoro-2',2'-dichloro-ethoxy)-phenyl]-N'- | wild | | | | | |

TABLE 1-continued

| Preparation containing | Test plant | Damage with kilograms of active ingredient per hectare | | | | |
|---|---|---|---|---|---|---|
| | | 10 kg/ha | 5 kg/ha | 2.5 kg/ha | 1.2 kg/ha | 0.6 kg/ha |
| methylurea | mustard | 100 % | 100 % | 100 % | 95 % | 75 % |
| N-[4-(1',1'-difluoro-2',2'-dichloro-ethoxy)-phenyl] N',N'-dimethylurea | " | 100 % | 100 % | 100 % | 90 % | 70 % |
| N-(4-chlorophenyl)-N'-methyl-N''-isobutinylurea | " | 100 % | 100 % | 100 % | 100 % | 80 % |
| N-[4-(1',1'-difluoro-2',2'-dichloro-ethoxy)-phenyl]-N'-methylurea | oat | 10 % | 0 % | 0 % | 0 % | 0 % |
| N-[4-(1',1'-difluoro-2',2'-dichloro-ethoxy)-phenyl]-N',N'-dimethylurea | " | 20 % | 10 % | 0 % | 0 % | 0 % |
| N-(4-chlorophenyl)-N'-methyl-N'-isobutinylurea | " | 100 % | 100 % | 90 % | 75 % | 50 % |

COMPARATIVE EXAMPLE 6

Cotton, wild mustard and wild oat were sown in pots in a greenhouse and 3 weeks after germination the pots were treated with an aqueous suspension of N-[4-(1',1'-dichlorovinyloxy)-phenyl]-N'-methylurea (preparation I) and a corresponding suspension of N-[4-(1',2'-dichlorovinyloxy)-phenyl]-N',N'-di-methylurea (preparation II), respectively. The respective wettable powders used for the preparation of the aqueous suspensions contained 25% of active ingredient and 75% of known additives.

As comparative substance N-(3-trifluoromethyl-phenyl)-N',N'-dimethylurea (preparation III) known as herbicide for cotton cultivations was used.

The results of the comparative test are indicated in Table 2. The results were evaluated 4 weeks after the treatment.

Preparations I and II containing the active ingredients according to the invention had a better effect on wild mustard than comparative substance III. With wild oat the effect of preparation II was almost equal to that of comparative preparation III, while the effect of preparation I was somewhat weaker. However, preparations I and II did less damage to the cotton. In a concentration of 1.2 kilograms/ha which destroys the wild mustard preparation III caused a brightening of the cotton leaves while higher concentrations partially involved slight necrosis. In contradistinction thereto, the herbicides according to the invention caused scarcely perceptible damages to the leaves (10% damage) only in 2 to 4 times higher concentrations.

The above results reveal that when cotton is treated after germination this crop plant is less damaged by the herbicides according to the invention with an about equal effect on the weeds.

COMPARATIVE EXAMPLE 7

In a greenhouse wild mustard, carrots, peas and kidney beans were sown in pots. On the day of sowing the soil was treated with an aqueous suspension of a wettable powder containing as active ingredient N-[4-(3',3'-dichloroallyloxy)-phenyl]-N'-methoxyurea (preparation IV) and N[4-(3',3'-di-chloroallyloxy)-phenyl]-N',N'-dimethylurea (preparation V), respectively. As comparative substance a chemically resembling urea derivative was used (cf. U.S. Pat. No. 2,655,447), i.e. N-(4-allyloxyphenyl)-N',N'-dimethylurea (preparation VI). All preparations contained 25% of active ingredient and 75% of usual additives in the form of a wettable powder.

The results were evaluated 5 weeks after the treatment. Particulars are indicated in Table 3.

Although all preparations used had about the same herbicidal effect on wild mustard, preparations IV and V according to the invention did must less damage to the three crop plants than comparative preparation VI. The difference was particularly evident with the effect of preparation IV on carrots. In a concentration of 1.2 kilograms/ha which killed the wild mustard the carrots did not suffer any damage while they were substantially destroyed with the same concentration of comparative preparation VI.

Preparation IV substantially saved the kidney beans in the indicated concentration and even with 4 times the concentration the degree of damage was only 30%. As compared herewith preparation VI when applied in a concentration of 1.2 kilograms/ha caused a slight to distinct damage of 20 to 40% whereas too high a concentration, which can never be avoided in practice, injured the plants to an extent of up to 90% with 5 kilograms per hectare.

TABLE 2

| Preparation | Test plant | Damage with kilograms of active ingredient per hectare | | | |
|---|---|---|---|---|---|
| | | 5 kg/ha | 2.5 kg/ha | 1.2 kg/ha | 0.6 kg/ha |
| I | Wild mustard | 100 % | 100 % | 100 % | 90 % |
| II | | 100 % | 100 % | 100 % | 100 % |
| III | | 100 % | 100 % | 100 % | 60 % |
| I | Wild oats | 75 % | 45 % | 30 % | 30 % |
| II | | 95 % | 75 % | 75 % | 50 % |
| III | | 95 % | 80 % | 75 % | 50 % |
| I | Cotton | 10 % | 10 % | 0 % | 0 % |
| II | | 10 % | 0 % | 0 % | 0 % |
| III | | 50 % | 40 % | 30 % | 10 % |

Preparation I = N-[4-(1',2'-dichlorovinyloxy)-phenyl]-N'-methylurea
Preparation II 32 N-[4-(1',2'-dichlorovinyloxy)-phenyl]-N'-dimethylurea
Preparation III = N-(3-trifluoromethyl-phenyl)-N',N'-dimethylurea It should be stressed that preparation V was particularly safe for peas whereas the action of preparation IV was a little less favorable. The comparative substance distinctly damaged the peas so that the practical use thereof is unsuitable. In this case, too, it can be seen that the novel herbicides are even tolerated in two to four times the usual concentration.

The above results reveal that with approximately the same herbicidal effect as the comparative substance, the herbicides according to the invention substantially save peas, carrots and kidney beans so that they are excellently suitable for the control of weeds in such crop plants.

N-[3-(1',1'-difluoro-2',2'-dichloroethoxy)-phenyl]-N'-methoxy-N'-methylurea (preparation VIII), respectively. As comparative substances various urea compounds and a triazine derivative were used, chosen according to the crop plants, namely:

N-3,4-dichlorophenyl-N'-methyl-N'-methoxyurea (linuron) (preparation IX) and 2-chloro-4,6-bis-ethylamino-s-triazine (simazin) (preparation X)

for pea, horse bean and the cereals,

N-4-chlorophenyl-N'-methyl-N'-isobutinylurea (buturon) (preparation XI)

for the cereals,

TABLE 3

| Test plant | Preparation | Damage with kg/ha of active ingredient | | | | | |
|---|---|---|---|---|---|---|---|
| | | 5 kg/ha | 2.5 kg/ha | 1.2 kg/ha | 0.6 kg/ha | 0.3 kg/ha | 0.15 kg/ha |
| Wild mustard | IV | 100 % | 100 % | 100 % | 95 % | 75 % | 30 % |
| | V | 100 % | 100 % | 100 % | 85 % | 45 % | 20 % |
| | VI | 100 % | 100 % | 100 % | 90 % | 70 % | 50 % |
| Carrot | IV | 40 % | 20 % | 0 % | 0 % | 0 % | 0 % |
| | V | 65 % | 50 % | 50 % | 20 % | 10 % | 10 % |
| | VI | 100 % | 100 % | 100 % | 80 % | 70 % | 50 % |
| Pea | IV | 30 % | 30 % | 20 % | 10 % | 0 % | 0 % |
| | V | 20 % | 20 % | 0 % | 0 % | 0 % | 0 % |
| | VI | 90 % | 80 % | 50 % | 30 % | 20 % | 20 % |
| Kidney bean | IV | 30 % | 20 % | 0 % | 0 % | 0 % | 0 % |
| | V | 50 % | 30 % | 20 % | 20 % | 0 % | 0 % |
| | VI | 90 % | 75 % | 40 % | 20 % | 20 % | 10 % |

Preparation IV = N-[4-(3',3'-dichloroallyloxy)-phenyl]-N'-methyl-N'-methoxyurea
Preparation V = N-[4-(3',3'-dichloroallyloxy)-phenyl]-N',N'-dimethylurea
Preparation VI = N-(4-allyloxyphenyl)-N',N'-dimethylurea

COMPARATIVE EXAMPLE 8

The dicotyledonous weeds
- wild mustard — Sinapis arvensis
- chickweed — Stellaria media
- field camomile — Anthemis arvensis
- and annual blackgrass — Alopecurus myosuroides and the crop plants
- pea — Pisum sativum
- horse bean — Vicia faba
- spring wheat — Triticum aestivum
- spring rye — Secale cereale
- spring barley — Hordeum distichum
- and cotton — Gossypium sp.

were sown in big plastics boxes filled with humous sandy loam and the boxes were covered. On the day of sowing the surface of the soil was treated with an aqueous suspension of a wettable powder containing as active ingredient N-[3-(1',1'-difluoro-2',2'-dichloroethoxy)-phenyl]-N',N'-dimethylurea (preparation VII) or N-3-trifluoromethylphenyl-N',N'-dimethylurea (fluometuron) (preparation XII)

and

N-3,4-dichlorophenyl-N',N'-dimethylurea (diuron) (preparation XIII) for cotton.

The boxes were placed in a hotbed and the results were evaluated 5 weeks after the treatment.

Table 4 shows that preparations VII and VIII according to the invention have, on the average, approximately the same effect on weeds as the indicated comparative substances, particularly on the dicotyledonous weeds. But also the foxtail grass still suffers a distinct damage. The destructive concentration for most of the weeds is about 0.6 kilogram of active ingredient per hectare for all preparations, i.e. the novel herbicides as well as the comparative substances.

Table 4

| Amount applied Preparation | Test plant | Damage with kg/ha of active ingredient | | | Test plant | | | |
|---|---|---|---|---|---|---|---|---|
| | | 0.15 kg/ha | 0.6 kg/ha | 2.5 kg/ha | | 0.15 kg/ha | 0.6 kg/ha | 2.5 kg/ha |
| VII | Wild mustard | 70% | 100% | 100 % | Chickweed | 90% | 100 % | 100% |
| VIII | | 60 % | 100 % | 100% | | 70% | 100% | 100% |
| IX | | 90% | 100% | 100% | | 100 % | 100% | 100% |
| X | | 80 % | 100 % | 100 % | | 90 % | 100 % | 100 % |
| XI | | 50 % | 70 % | 100 % | | 70 % | 100 % | 100 % |
| XII | | 60 % | 100 % | 100 % | | 90 % | 100 % | 100 % |
| XIII | | 50 % | 80 % | 100 % | | 80 % | 100 % | 100 % |
| VII | Field camomile | 60 % | 100 % | 100 % | Foxtail grass | 30 % | 60 % | 90 % |
| VIII | | 50 % | 90 % | 100 % | | 10 % | 40 % | 60 % |
| IX | | 80 % | 100 % | 100 % | | 30 % | 60 % | 80 % |
| X | | 60 % | 100 % | 100 % | | 50 % | 80 % | 100 % |
| XI | | 70 % | 100 % | 100 % | | 60 % | 80 % | 100 % |
| XII | | 80 % | 100 % | 100 % | | 10 % | 40 % | 60 % |
| XIII | | 80 % | 100 % | 100 % | | 30 % | 60 % | 80 % |

Table 5 shows, however, that the novel herbicides are distinctly safer for some crop plants than the comparative substances. Pea, horse bean as well as cotton were not damaged or damaged to a very small extent only by 0.6 kilogram per hectare of the preparations according to the invention, whereas the same amount of the corresponding comparative substances injured the specified plants to a lesser or greater extent. The selectivity was especially pronounced when surplus amounts were applied as it is relatively often the case in practice. With 4 times the normal concentration, that is to say 2.5 kilograms per hectare, the horse bean exhibited some damage whereas cotton and pea remained practically undamaged. The comparative substances caused much more serious damages, above all preparations IX and X on the pea. Even 16 times the concentration (10 kg/ha) of the novel compounds hardly damaged cotton

| kidney bean | Phaseolus vulgaris |
|---|---|

Table 6 shows that the novel herbicides XIV and XV exhibited a good effect on dicotyledonous weeds such as wild mustard and chickweed, and did not injur a series of crop plants. Even when applied in double the concentration they caused at most a minor damage, if any.

Table 6

| Amount applied preparation | Damage with kilograms active ingredient per hectare | | | | | | | | |
|---|---|---|---|---|---|---|---|---|---|
| | Test plant: wild mustard | | | Test plant: chickweed | | | Test plant: pea | | |
| | 1.2 kg/ha | 2.5 kg/ha | 5 kg/ha | 1.2 kg/ha | 2.5 kg/ha | 5 kg/ha | 1.2 kg/ha | 2.5 kg/ha | 5 kg/ha |
| XIV | 70 % | 100 % | 100 % | 70% | 100 % | 100 % | 0 % | 0 % | 20 % |
| XV | 90 % | 100 % | 100 % | 100 % | 100 % | 100 % | 0 % | 0 % | 20 % |

| | Test plant: oat | | | Test plant: barley | | | Test plant: wheat | | |
|---|---|---|---|---|---|---|---|---|---|
| | 1.2 kg/ha | 2.5 kg/ha | 5 kg/ha | 1.2 kg/ha | 2.5 kg/ha | 5 kg/ha | 1.2 kg/ha | 2.5 kg/ha | 5 kg/ha |
| XIV | 0 % | 0 % | 20 % | 0 % | 0 % | 10 % | 0 % | 0 % | 10 % |
| XV | 0 % | 0 % | 30 % | 0 % | 0 % | 0 % | 0 % | 0 % | 0 % |

| | Test plant: sorghum millet | | | Test plant: maize | | | Test plant: bean | | |
|---|---|---|---|---|---|---|---|---|---|
| | 1.2 kg/ha | 2.5 kg/ha | 5 kg/ha | 1.2 kg/ha | 2.5 kg/ha | 5 kg/ha | 1.2 kg/ha | 2.5 kg/ha | 5 kg/ha |
| XIV | 0 % | 0 % | 0 % | 0 % | 0 % | 10 % | 0 % | 20 % | 40 % |
| XV | 0 % | 0 % | 0 % | 0 % | 0 % | 0 % | 0 % | 0 % | 20 % | and pea, whereas the same concentrations of the comparative substances strongly injured the cotton and completely destroyed the pea.

Moreover, under practical conditions preparation VIII had a much better selectivity in cultivations of various cereals (wheat, rye, barley) than the comparative substances.

COMPARATIVE EXAMPLE 10

In a field test on loamy soil peas and horse beans were treated on the day of sowing with an aqueous suspension of N-[4-(2'-chloroethoxy)-phenyl]-N',N'-dimethylurea (XVI)

Table 5

| Amount applied preparation | Test plant: pea | | | | Test plant: horse bean | | | | Test plant: cotton | | | |
|---|---|---|---|---|---|---|---|---|---|---|---|---|
| | 0.15 kg/ha | 0.6 kg/ha | 2.5 kg/ha | 10.0 kg/ha | 0.15 kg/ha | 0.6 kg/ha | 2.5 kg/ha | 10.0 kg/ha | 0.15 kg/ha | 0.6 kg/ha | 2.5 kg/ha | 10.0 kg/ha |
| VII | 0% | 0% | 10% | 30 % | 0 % | 20 % | 50 % | 90 % | 0 % | 0 % | 0 % | 10 % |
| VIII | 0 % | 0 % | 10 % | 30 % | 0 % | 0 % | 20 % | 50 % | 0 % | 0 % | 10 % | 20 % |
| IX | 0 % | 20 % | 60 % | 100 % | 0 % | 40 % | 70 % | 100 % | | | | |
| X | 0 % | 30 % | 60 % | 100 % | 0 % | 20 % | 60 % | 100 % | | | | |
| XII | | | | | | | | | 0 % | 10 % | 30 % | 50 % |
| XIII | | | | | | | | | 0 % | 10 % | 30 % | 60 % |

| | Test plant: wheat | | | | Test plant: rye | | | | Test plant: barley | | | |
|---|---|---|---|---|---|---|---|---|---|---|---|---|
| | 0.15 kg/ha | 0.6 kg/ha | 2.5 kg/ha | 10.0 kg/ha | 0.15 kg/ha | 0.6 kg/ha | 2.5 kg/ha | 10.0 kg/ha | 0.15 kg/ha | 0.6 kg/ha | 2.5 kg/ha | 10.0 kg/ha |
| VIII | 0 % | 0 % | 20 % | 40 % | 0 % | 0 % | 30 % | 60 % | 0 % | 0 % | 20 % | 30 % |
| IX | 0 % | 30 % | 70 % | 100 % | 10 % | 50 % | 90 % | 100 % | 0 % | 10 % | 30 % | 70 % |
| X | 20 % | 70 % | 90 % | 100 % | 0 % | 50 % | 80 % | 100 % | 30 % | 70 % | 100 % | 100 % |
| XI | 10 % | 50 % | 70 % | 100 % | 0 % | 40 % | 90 % | 100 % | 0 % | 30 % | 70 % | 100 % |

COMPARATIVE EXAMPLE 9

In the same manner as in Comparative Example 8 the substances

N-[3-(1',1'-difluoro-2',2'-dichloroethoxy)-phenyl]-N'-methoxyurea (preparation XIV) and N-[3-(1',1'-difluoro-2',2'-dichloroethoxy)-phenyl]-N'-methylurea (preparation XV) were tested as to their effect on wild mustard, chickweed, pea, spring wheat and spring barley and additionally on N-[4-(2'-chloroethoxy)-phenyl]-N'-methyl-N'-methoxyurea (XVII)

N-[4-(2'-chloroethoxy)-phenyl]-N'-methylurea (XVIII), respectively. Each plot had a size of 20 square meters. Each suspension was applied to 4 plots. The comparative substance was a urea preparation on the basis of N-[4-(p-chlorophenoxy)-phenyl]-N',N'-dimethylurea (chloroxuron, XIX) often used for various vegetable cultivations.

The data of the evaluation 8 weeks later by visual inspection are calculated to give the degree of damage in percent.

As weeds the following dicotyledonous types were present:

| oat | Avena sativa |
|---|---|
| sorghum millet | Sorghum millet |
| maize | Zea mays |

| chickweed | Stellaria media |
|---|---|

-continued

| | |
|---|---|
| shepherd's purse | Capsella bursa-pastoris |
| dead nettle | Lamium amplexicaule |
| groundsel | Senecio vulgaris |
| wild mustard | Sinapis arvensis and |
| knotweed | Polygonum aviculare |

The results of the evaluation of these types are indicated. As monocotyledonous weed
annual blackgrass    Alopecurus myosuroides
was present.

Table 7 shows that the action on dicotyledonous weeds of two of the substances according to the invention, namely XVI and XVII, was slightly superior to that of comparison substance XIX, while the action of the third compound XVIII was approximately equal to that of the latter. The novel herbicides had, however, a distinctly better effect on the often cumbersome annual blackgrass. Moreover, the results indicate that all three novel preparations were less harmful to the pea, whereas at least two of the three compounds, namely XVI and XVIII were distinctly safer for the horse bean than the comparative substance.

The advantage of the compounds according to the invention is therefore based on the fact that they are safer for peas and horse beans than known herbicides and, moreover, that they control more effectively weedy grasses such as annual blackgrass.

and the following crop plants

| | |
|---|---|
| pea | Pisum sativum |
| horse bean | Vicia faba |
| kidney bean | Phaseolus vulgaris |
| carrot | Daucus carota |
| spring rye | Secale cereale |
| spring barley | Hordeum distichum |
| spring wheat | Triticum aestivum |
| oat | Avena sativa |
| maize | Zea mays |
| rice | Oryza sativa and |
| cotton | Gossypium sp. | were sown in boxes filled with humous sandy loam. The surface of the soil was sprayed on the same day with aqueous suspensions of the specified preparations. After 5 weeks the plants were classified by visual inspection and the values obtained were calculated to give the degree of damage in percent. As comparative substances the following compounds were used:

for cotton: N-3,4-dichlorophenyl-N',N'-dimethylurea (diuron, IV)

for the vegetables: N-4-(p-chlorophenoxy)-phenyl-N',N'-dimethylurea (chloroxuron, V)

for the cereals: N-4-chlorophenyl-N'-methyl-N'-methoxyurea (monolinuron, VI)

Table 8 shows that the compounds according to the invention I, II and III have approximately the same effect on the germinating dicotyledonous weeds as the Table 7

| preparation | Test plant | 1.25 kg/ha | 2.5 kg/ha | 5.0 kg/ha | Test plant | 1.25 kg/ha | 2.5 kg/ha | 5.0 kg/ha |
|---|---|---|---|---|---|---|---|---|
| XVI | Dicotylous weed | 90 % | 98 % | 100 % | Pea | 0 % | 10 % | 20 % |
| XVII | | 90 % | 98 % | 100 % | | 0 % | 0 % | 10 % |
| XVIII | | 60 % | 73 % | 95 % | | 0 % | 0 % | 10 % |
| XIX | | 65 % | 85 % | 98 % | | 20 % | 30 % | 40 % |
| XVI | Annual blackgrass | 60 % | 80 % | 90 % | Horse bean | 0 % | 10 % | 10 % |
| XVII | | 60 % | 70 % | 80 % | | 0 % | 10 % | 30 % |
| XVIII | | 40 % | 50 % | 60 % | | 0 % | 0 % | 0 % |
| XIX | | 0 % | 20 % | 30 % | | 0 % | 20 % | 30 % |

COMPARATIVE EXAMPLE 11

In a hotbed the following compounds
N-[3-chloro-4-(1',1'-difluoro-2',2'-dichloroethoxy)-phenyl]-N'-methylurea (preparation I)
N-[3-chloro-4-(1',1'-difluoro-2',2'-dichloroethoxy)-phenyl]-N',N'-dimethylurea (preparation II) and
N-[3-chloro-4-(1',1'-difluoro-2',2'-dichloroethoxy)-phenyl]-N'-methyl-N'-methoxyurea (III)
were tested as to their herbicidal effect and safety in a series of crop plants. The seeds of the following weeds

| | |
|---|---|
| wild mustard | Sinapis arvensis |
| chickweed | Stellaria media |
| field camomile | Anthemis arvensis |
| groundsel | Senecio vulgaris | known comparative substances. The concentration sufficient for a normal control of the weeds is, in general, in the range of from 0.6 to 1.2 kilograms of active ingredient per hectare.

Table 9 indicates, however, that the novel herbicides are safer for the crop plants. Compounds I and II are safer for cotton, pea, horse bean and kidney bean, compound II is safer for the carrot and all three novel compounds are safer for the cereals than the comparative substances. Even when applied in a surplus concentration the novel compounds only involve little damage.

Hence, it follows that the compounds according to the invention are distinctly safer, above all for cotton and kidney beans, furthermore for rye, oat, maize and a series of other crop plants than the corresponding comparative substances.

Table 8

| preparation | Test plant | 0.6 kg/ha | 1.2 kg/ha | 5.0 kg/ha | Test plant | 0.6 kg/ha | 1.2 kg/ha | 5.0 kg/ha |
|---|---|---|---|---|---|---|---|---|
| I | Wild mustard | 50 % | 60 % | 95 % | Chick weed | 70 % | 85 % | 100 % |
| II | | 80 % | 95 % | 100 % | | 100 % | 100 % | 100 % |
| III | | 80 % | 90 % | 90 % | | 90 % | 90 % | 100 % |
| IV | | 80 % | 100 % | 100 % | | 100 % | 100 % | 100 % |
| V | | 60 % | 80 % | 90 % | | 70 % | 80 % | 100 % |
| VI | | 75 % | 90 % | 100 % | | 90 % | 100 % | 100 % |

Table 8-continued

| Amount applied preparation | Test plant | Degree of damage with kilograms of active ingredient per hectare | | | Test plant | 0.6 kg/ha | 1.2 kg/ha | 5.0 kg/ha |
|---|---|---|---|---|---|---|---|---|
| | | 0.6 kg/ha | 1.2 kg/ha | 5.0 kg/ha | | | | |
| I | Field camomile | 70 % | 85 % | 95 % | Groundsel | 80 % | 90 % | 100 % |
| II | | 80 % | 95 % | 100 % | | 90 % | 100 % | 100 % |
| III | | 60 % | 70 % | 100 % | | 80 % | 90 % | 95 % |
| IV | | 90 % | 100 % | 100 % | | 100 % | 100 % | 100 % |
| V | | 75 % | 85 % | 100 % | | 70 % | 80 % | 95 % |
| VI | | 80 % | 95 % | 100 % | | 90 % | 100 % | 100 % |

Table 9

| Amount applied preparation | Test plant | 0.6 kg/ha | 1.2 kg/ha | 5.0 kg/ha | Action on cultivated plants Preparation | Test plant | 0.6 kg/ha | 1.2 kg/ha | 5.0 kg/ha |
|---|---|---|---|---|---|---|---|---|---|
| I | Cotton | 0 % | 0 % | 0 % | I | Carrots | 0 % | 10 % | 40 % |
| II | | 0 % | 0 % | 0 % | II | | 0 % | 0 % | 10 % |
| IV | | 10 % | 30 % | 40 % | V | | 0 % | 20 % | 40 % |

| Preparation | Test plant: pea | | | Test plant: horse bean | | | Test plant: kidney bean | | |
|---|---|---|---|---|---|---|---|---|---|
| | 0.6 kg/ha | 1.2 kg/ha | 5.0 kg/ha | 0.6 kg/ha | 1.2 kg/ha | 5.0 kg/ha | 0.6 kg/ha | 1.2 kg/ha | 5.0 kg/ha |
| I | 0. % | 0 % | 10 % | 0 % | 0 % | 10 % | 0 % | 0 % | 0 % |
| II | 0 % | 0 % | 20 % | 0 % | 0 % | 30 % | 0 % | 0 % | 0 % |
| V | 10 % | 30 % | 40 % | 20 % | 20 % | 40 % | 0 % | 20 % | 55 % |

| Preparation | Test plant: rye | | | Test plant: barley | | | Test plant: wheat | | |
|---|---|---|---|---|---|---|---|---|---|
| | 0.6 kg/ha | 1.2 kg/ha | 5.0 kg/ha | 0.6 kg/ha | 1.2 kg/ha | 5.0 kg/ha | 0.6 kg/ha | 1.2 kg/ha | 5.0 kg/ha |
| I | 0 % | 0 % | 0 % | 0 % | 0 % | 20 % | 0 % | 0 % | 0 % |
| II | 0 % | 0 % | 30 % | 0 % | 20 % | 25 % | 0 % | 0 % | 10 % |
| III | 0 % | 0 % | 30 % | 0 % | 30 % | 40 % | 0 % | 0 % | 20 % |
| VI | 30 % | 80 % | 100 % | 30 % | 60 % | 90 % | 40 % | 70 % | 100 % |

| Preparation | Test plant: oat | | | Test plant: maize | | | Test plant: rice | | |
|---|---|---|---|---|---|---|---|---|---|
| | 0.6 kg/ha | 1.2 kg/ha | 5.0 kg/ha | 0.6 kg/ha | 1.2 kg/ha | 5.0 kg/ha | 0.6 kg/ha | 1.2 kg/ha | 5.0 kg/ha |
| I | 0 % | 0 % | 10 % | 0 % | 0 % | 0 % | 0 % | 0 % | 10 % |
| II | 0 % | 0 % | 10 % | 0 % | 0 % | 10 % | 0 % | 10 % | 20 % |
| III | 0 % | 0 % | 0 % | 0 % | 0 % | 0 % | 0 % | 10 % | 30 % |
| VI | 30 % | 60 % | 100 % | 20 % | 30 % | 50 % | 30 % | 50 % | 90 % |

COMPARATIVE EXAMPLE 12

N-[3-methyl-4-(1',1'-difluoro-2',2'-dichloroethoxy)-phenyl]-N'-methyl-N'-methoxyurea (VII),
N-[3-methyl-4-(1',1'-difluoro-2',2'-dichloroethoxy)-phenyl]-N',N'-dimethylurea (VIII),
N-4-chlorophenyl-N'-methyl-N'-methoxyurea (monolinuron, IX)
N-4-chlorophenyl-N'-methyl-N'-isobutinylurea (buturon, X) mixed product of 5% of 2-chloro-3,6-bisethylamino-s-triazin (simazin) and 22.5% of 2-methylmercapto-4-isopropylamino-6-(3'-methoxy)-propylamino-s-triazine (XI) were tested as follows:

| | |
|---|---|
| wild mustard | Sinapis arvensis |
| chickweed | Stellaria media |
| field camomile | Anthemis arvensis |
| fat hen | Chenopodium album |
| and the crop plants | |
| spring wheat | Triticum aestivum |
| spring barley | Hordeum distichum |
| oats | Avena sativa |
| rice | Oryza sativa |
| sugar beet | Beta vulgaris and |
| horse bean | Vicia faba | were sown in boxes filled with humous sandy loam. On the same day the surface of the soil was sprayed with an aqueous suspension of preparations VII and VIII. As comparative substances two urea compounds often used for cereals (XI and X) and a mixed triazine product also suitable for cereals were used. Comparative product IX is also suitable for horse beans.

After the treatment the boxes were placed in a hotbed and kept therein for 6 weeks until the test was evaluated. Table 10 shows that the novel compounds VII and VIII had about the same action on weeds as the comparative substances. With an amount applied of 1.2 kilograms per hectare of active ingredient the latter killed all weeds whereas the same amount of the novel compounds strongly damaged the weeds and a higher amount fully destroyed the weeds.

Table 10

| | Degree of damage on weeds with | | |
|---|---|---|---|
| Preparation | 0.6 kg/ha | 1.2 kg/ha | 2.5 kg/ha |
| VII | 54 % | 73 % | 100 % |
| VIII | 76 % | 89 % | 100 % |
| IX | 92 % | 99 % | 100 % |
| X | 92 % | 100 % | 100 % |
| XI | 90 % | 100 % | 100 % |

The indicated values are average values for all four types of weeds.

The following Table 11 reveals, however, that with an amount of 1.2 kg/ha the comparative substances strongly or very strongly injured the cereals mentioned, whereas the novel compounds saved completely or almost completely wheat, barley, oat and rice in an amount of 1.2 and 2.5 kg/ha. Furthermore, the horse bean was not or only slightly damaged by the novel compounds, whereas comparative substance IX strongly damaged this type of plant. Novel substance VII saved the sugar beet when applied in the indicated amount, whereas all comparative substances destroyed the beet almost completely.

The novel compounds have the advantage that in an amount sufficient to destroy or strongly injure a series of important field weeds they save numerous crop plants such as wheat, barley, oat, rice and horse bean, partially also sugar beet, whereas comparative substances often used for the indicated cultivations exhibit a much stronger damaging action.

-continued

| | Degree of damage in percent (100 = complete destruction - 0 = no damage) | | | | | |
|---|---|---|---|---|---|---|
| | I | | II | | comparative substance | |
| | 0.3 | 0.6 | 0.3 | 0.6 | 0.3 | 0.6 |
| carrot | 0 | 10 | 0 | 0 | 30 | 50 |

The novel compounds and the comparative substance showed an excellent herbicidal effect. The novel Table 11

| | Action on crop plants | | | | | | | | |
|---|---|---|---|---|---|---|---|---|---|
| | Test plant: wheat | | | Test plant: barley | | | Test plant: oat | | |
| Preparation | 0.6 kg/ha | 1.2 kg/ha | 2.5 kg/ha | 0.6 kg/ha | 1.2 kg/ha | 2.5 kg/ha | 0.6 kg/ha | 1.2 kg/ha | 2.5 kg/ha |
| VII | 0 % | 0 % | 0 % | 0 % | 0 % | 0 % | 0 % | 0 % | 0 % |
| VIII | 10 % | 10 % | 20 % | 0 % | 0 % | 30 % | 0 % | 0 % | 10 % |
| IX | 20 % | 50 % | 95 % | 20 % | 40 % | 50 % | 40 % | 80 % | 100 % |
| X | 65 % | 80 % | 90 % | 55 % | 95 % | 100 % | 60 % | 90 % | 100 % |
| XI | 85 % | 90 % | 100 % | 70 % | 90 % | 100 % | 80 % | 85 % | 100 % |

| | Test plant: rice | | | Test plant: sugar beet | | | Test plant: horse bean | | |
|---|---|---|---|---|---|---|---|---|---|
| Preparation | 0.6 kg/ha | 1.2 kg/ha | 2.5 kg/ha | 0.6 kg/ha | 1.2 kg/ha | 2.5 kg/ha | 0.6 kg/ha | 1.2 kg/ha | 2.5 kg/ha |
| VII | 0 % | 0 % | 0 % | 0 % | 0 % | 20 % | 0 % | 0 % | 0 % |
| VIII | 0 % | 0 % | 0 % | 100 % | 100 % | 100 % | 0 % | 10 % | 20 % |
| IX | 80 % | 95 % | 100 % | 95 % | 100 % | 100 % | 50 % | 60 % | 80 % |
| X | 40 % | 55 % | 70 % | 100 % | 100 % | 100 % | | | |
| XI | 70 % | 80 % | 90 % | 100 % | 100 % | 100 % | | | |

COMPARATIVE EXAMPLE 13

In a greenhouse the following weeds
| | |
|---|---|
| wild mustard | Sinapis arvensis |
| chickweed | Stellaria media |
| field camomile | Anthemis arvensis |
| barnyard grass | Echinochloa crus-galli |
| annual meadow grass | Poa annua |
| and the crop plants | |
| maize | Zea mays |
| wheat | Triticum sativum |
| horse bean | Vicia faba |
| pea | Pisum sativum |
| carrot | Daucus carota | were sown in boxes filled with humous sandy loam. On the same day the surface of the soil was sprayed with wettable powders suspended in water of the following compounds of the invention I. N-[3-chloro-4-(2'-chloroethoxy)-phenyl]-N',N'-dimethyl-urea (cf. Example 138) and
II. N-[3-trifluoromethyl-4-(2'-chloroethoxy)-phenyl]-N',N'-dimethyl-urea (cf. Example 144)

As comparative substance the known urea derivative fluometuron = N-3-trifluoromethylphenyl-N',N'-dimethyl-urea was used.

The evaluation after 6 weeks with concentrations of 0.3 and 0.6 kilogram of active ingredient per hectare gave the following results:

| | Degree of damage in percent (100 = complete destruction - 0 = no damage) | | | | | |
|---|---|---|---|---|---|---|
| | I | | II | | comparative substance | |
| | 0.3 | 0.6 | 0.3 | 0.6 | 0.3 | 0.6 |
| weeds (average of 5 types) | 90 | 100 | 92 | 99 | 92 | 99 |
| maize | 0 | 0 | 0 | 0 | 20 | 60 |
| wheat | 0 | 0 | 0 | 0 | 40 | 70 |
| horse bean | 0 | 0 | 0 | 0 | 60 | 90 |
| pea | 0 | 0 | 0 | 0 | 25 | 70 | compounds did no harm to the crop plants maize, wheat, horse bean, pea and carrot, which plants were strongly or very strongly injured by the comparative substance.

COMPARATIVE EXAMPLE 14

In a further test and in the same manner as described in comparative Example 1, the five types of weeds and as crop plants maize and cotton (Gossypium sp.) were sown. The surface of the soil was sprayed with a wettable powder suspended in water and containing as active ingredient III. N-[3-chloro-4-(2'-chloroethoxy)-phenyl]-N'-methyl-N'-methoxy-urea (cf. Example 140).

As comparative substance the chemically closely related urea herbicide N-(3-chloro-4-methoxyphenyl)-N'-methyl-N'-methoxy-urea was used.

The evaluation after 6 weeks with concentrations of 0.6 and 1.2 kilograms of active ingredient per hectare gave the following result:

| | Degree of damage in percent | | | |
|---|---|---|---|---|
| | III | | comparative substance | |
| | 0.6 | 1.2 | 0.6 | 1.2 |
| weeds (average of 5 types) | 80 | 96 | 76 | 86 |
| maize | 0 | 0 | 30 | 50 |
| cotton | 0 | 10 | 60 | 100 |

The herbicidal effect of compound III was approximately equal to that of the comparative substance but the novel compound did no harm to the crop plants maize and cotton which were strongly damaged and partly even destroyed by the comparative substance.

COMPARATIVE EXAMPLE 15

In boxes filled with humous sandy loam, spring wheat (Triticum aestivum) and spring barley (Hordeum distichum) were sown together with the weeds wild oat (*Avena fatua*) and various broad-leaved types (*Sinapis arvensis, Stellaria media, Galium aparine, Anthemis arvensis, Veronica arvensis* and *Polygonum persicaria*). On the same day the surface of the soil was sprayed with aqueous suspensions of the compounds of the invention IV. N-[3-methyl-4-(2'-chloroethoxy)-phenyl]-N',N'-dimethylurea (cf. Example 148) and V. N-[3-methyl-4-(2'-chloroethoxy)-phenyl]-N'-methyl-N'-methoxyurea (cf. Example 149) As comparative compound the triazine derivatives known as herbicide for cereals 2-methylmercapto-4-ethylamino-6-tert.butyl-amino-s-triazine was used.

The evaluation after 5 weeks with concentrations of 0.6 kilogram of active ingredient per hectare gave the following result:

| Degree of damage in percent (100 = complete destruction 0 = no damage) | | | |
|---|---|---|---|
| type of plant | IV | V | comparative substance |
| wheat | 10 | 0 | 0 |
| barley | 0 | 0 | 0 |
| weeds | | | |
| wild oat | 100 | 100 | 20 |
| other weeds (average value) | 94 | 86 | 92 |

The table shows that all preparations had a good or very good action against broad-leaved weeds and did no harm to cereals. But the very cumbersome wild oat which is difficult to combat was not damaged by the known herbicide for cereals whereas the compounds of the invention destroyed the wild oat without doing any harm to the botanically closely related cereals wheat and barley.

What we claim is:

1. A herbicidal preparation containing an effective amount of

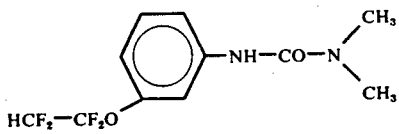

as the active ingredient, in combination with an inert solid or liquid carrier, a solvent, adhesive, wetting agent, dispersing agent or grinding auxiliary.

2. A preparation as claimed in claim 1 in the form of a wettable powder.

3. A preparation as claimed in claim 1 in the form of a solution or emulsion concentrate.

4. The method of selectively controlling weeds in cotton which comprises applying a herbicidal preparation as in claim 1 to the locus thereof in a concentration which strongly damages said weeds and saves the cotton.

* * * * *